United States Patent [19]

Chen

[11] Patent Number: 4,782,050
[45] Date of Patent: Nov. 1, 1988

[54] 6-BETA(SUBSTITUTED)-(S)-HYDROXYME-THYLPENICILLANIC ACIDS AND DERIVATIVES THEREOF

[75] Inventor: Yuhpyng L. Chen, Waterford, Conn.

[73] Assignee: Pfizer Inc., New York, N.Y.

[21] Appl. No.: 128,665

[22] Filed: Dec. 4, 1987

Related U.S. Application Data

[63] Continuation-in-part of Ser. No. 7,319, Jan. 27, 1987, abandoned.

[51] Int. Cl.$^4$ ................. C07D 499/00; A61K 31/425
[52] U.S. Cl. .................................... 514/192; 514/193; 540/310
[58] Field of Search ................ 540/310; 514/192, 193

[56] References Cited

U.S. PATENT DOCUMENTS 4,287,181 9/1981 Kellogg ............................... 424/114
4,503,040 3/1985 Barth ................................. 540/310

Primary Examiner—Nicholas S. Rizzo
Attorney, Agent, or Firm—Peter C. Richardson; J. Trevor Lumb; James M. McManus

[57] ABSTRACT

Antibacterial penicillins of the formula

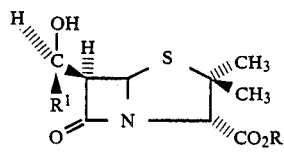

or a pharmaceutically acceptable salt thereof wherein $R^1$ is a heterocyclic group and R is hydrogen, the residue of certian carboxy protecting groups or the residue of an ester group readily hydrolyzable in vivo having activity against resistant organisms.

27 Claims, No Drawings

6-BETA(SUBSTITUTED)-(S)-HYDROXYMETHYL-PENICILLANIC ACIDS AND DERIVATIVES THEREOF

CROSS REFERENCE TO RELATED APPLICATIONS

This application is a continuation-in-part of copending application Ser. No. 7319 filed Jan. 27, 1987, now abandoned.

BACKGROUND OF THE INVENTION

The invention relates to novel 6-(substituted)hydroxymethylpenicillanic acids, certain esters and pharmaceutically acceptable salts thereof, pharmaceutical compositions containing them and their use as antibacterial agents and intermediates therefor.

One of the most well-known and widely used of the classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of commo cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin, it can increase or enhance the antibacterial effectiveness of the penicillin or cephalosporin against certain microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components.

The 6-beta-(substituted)-(S)-hydroxymethylpenicillanic acids and certain ester derivatives of the present invention are unique in that they possess outstanding antibacterial activity against resistant microorganisms, indicating that these compounds also possess the ability to inhibit the beta-lactamase of these organisms.

U.S. Pat. No. 4,287,181 discloses certain 6-substituted penicillanic acid 1,1-dioxides and esters thereof wherein the 6-substituent is

and, inter alia, $R_3$ is H or alkanoyl and $R_4$ is H, ($C_1$-$C_4$)alkyl, phenyl, benzyl or pyridyl, which are useful as beta-lactamase inhibitors.

SUMMARY OF THE INVENTION

The present invention provides antibacterial 6-beta-(substituted)-(S)-hydroxymethylpenicillanic acids of the formula

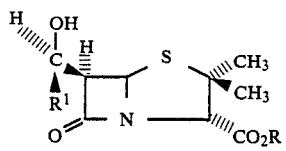

and a pharmaceutically acceptable salt thereof wherein $R^1$ is

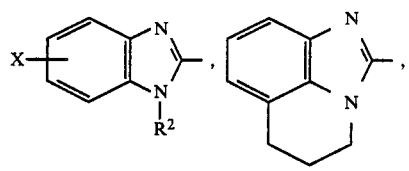

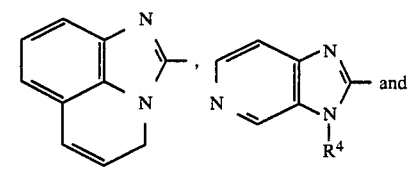

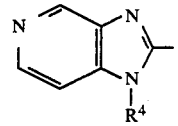

where $R^2$ is phenyl, vinyl, allyl, cyclopropyl, propargyl, fluoromethyl, 2-fluoroethyl, 2-hydroxyethyl, methoxy, methoxymethyl, 2-methoxyethyl, methylthiomethyl or 2-thienylmethyl; $R^4$ is vinyl, allyl or alkyl of one to three carbon atoms; X is hydrogen, methyl, methoxy or fluoro; and R is hydrogen, benzyl, allyl and the residue of an ester group readily hydrolyzable in vivo selected from 3-phthalidyl, 4-crotonolactonyl, gamma-butyrolacton-4-yl,

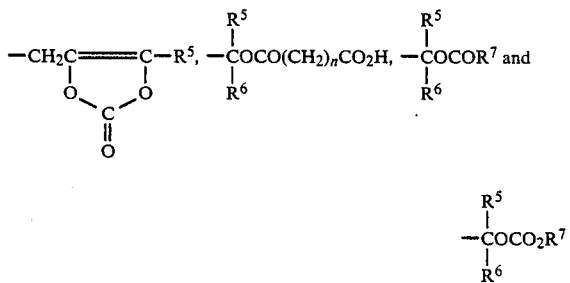

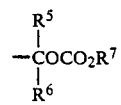

where $R^5$ and $R^6$ are each hydrogen or alkyl of one to two carbon atoms, n is 1 to 5 and $R^7$ is alkyl of one to six carbon atoms.

A preferred group of compounds are those where R hu 1 is

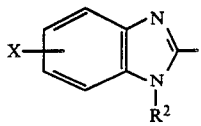

where X and R are each hydrogen. Especially preferred within this group are compounds where $R^2$ is vinyl, propargyl, methylthiomethyl, allyl, 2-fluoroethyl, fluoromethyl, cyclopropyl, methoxymethyl, 2-methoxyethyl, 2-hydroxyethyl, 2-thienylmethyl or methoxy.

A second preferred class of compounds is where $R^1$ is

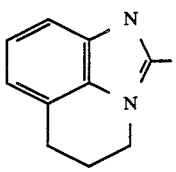

and R is hydrogen.

A third preferred class of compounds, is where $R^1$ is

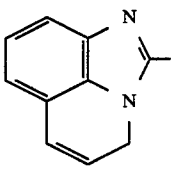

and R is hydrogen.

Also considered part of the present invention is a method for treating a bacterial infection in a mammalian subject which comprises administering to said subject an antibacterially effective amount of a compound of the formula

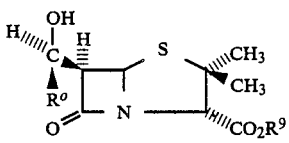

and a pharmaceutically acceptable salt thereof wherein $R°$ is

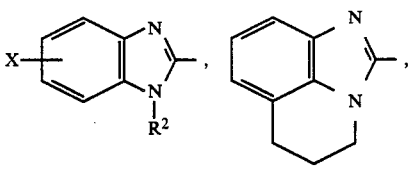

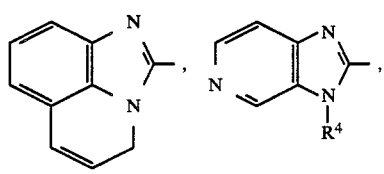

where $R^2$ is phenyl, vinyl, allyl, cyclopropyl, fluoromethyl, 2-fluoroethyl, 2-hydroxyethyl, methoxy, propargyl, methoxymethyl, 2-methoxyethyl, methylthiomethyl or 2-thienylmethyl; $R^3$ is phenyl or vinyl; $R^4$ is vinyl, allyl or alkyl of one to three carbon atoms; X is hydrogen, methyl, methoxy or fluoro; $R^8$ is hydrogen or alkyl of one to three carbon atoms; and $R^9$ is hydrogen or the residue of an ester group readily hydrolyzable in vivo selected from 3-phthalidyl, 4-crotonolactonyl, gamma-butyrolacton-4-yl,

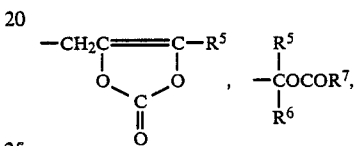

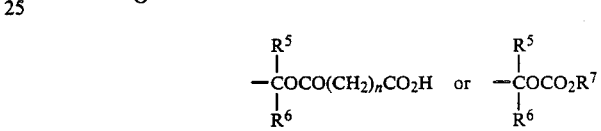

where $R^5$ and $R^6$ are each hydrogen or alkyl of one to two carbon atoms, n is 1 to 5 and $R^7$ is alkyl of one to six carbon atoms.

Of special interest are compounds where $R°$ is

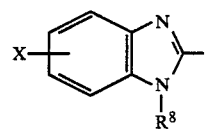

and X and $R^9$ are each hydrogen. Preferred are those compounds where $R^8$ is ethyl or n-propyl.

A second group of preferred compounds are those wherein $R°$ is

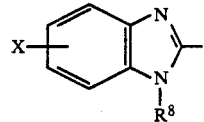

$R^9$ is hydrogen and $R^8$ is methyl. Preferred within this group are compounds where X is hydrogen, 5-, 6- or 7-methyl, 5-methoxy or 5-fluoro.

Since the compounds of the present invention contain a basic nitrogen in the groups represented by $R°$ and $R^1$, they are capable of forming acid addition salts. Such salts with pharmaceutically acceptable acids are included in the invention. Examples of such acids are hydrochloric, hydrobromic, sulfuric, phosphoric, citric, malic, tartaric, maleic, fumaric, gluconic, saccharic, benzenesulfonic, p-toluenesulfonic, p-chlorobenzenesulfonic and 2-naphthalenesulfonic acids.

Further, the compounds of the instant invention wherein R or $R^9$ are hydrogen form cationic salts and such salts with pharmaceutically acceptable cations are included in the invention. Examples of such cations are sodium, potassium, ammonium, calcium, magnesium, zinc; and substituted ammonium salts formed with amines such as diethanolamine, choline, ethylenediamine, ethanolamine, N-methylglucamine and procaine.

DETAILED DESCRIPTION OF THE INVENTION

The compounds of the invention are prepared by the following general method:

Suitable solvents for use with the organotin hydride reducing agents are those which substantially dissolve the starting compound of formula 2 but do not themselves react with the hydride reducing agent. Examples of such solvents include the aromatic hydrocarbons such as benzene, toluene, xylene, chlorobenzene and napthalene; and ethers such as ethyl ether, isopropyl ether, tetrahydrofuran, dioxane and 1,2-dimethoxyethane. Particularly preferred solvents for reasons of economy and efficiency are benzene, tetrahydrofuran and toluene.

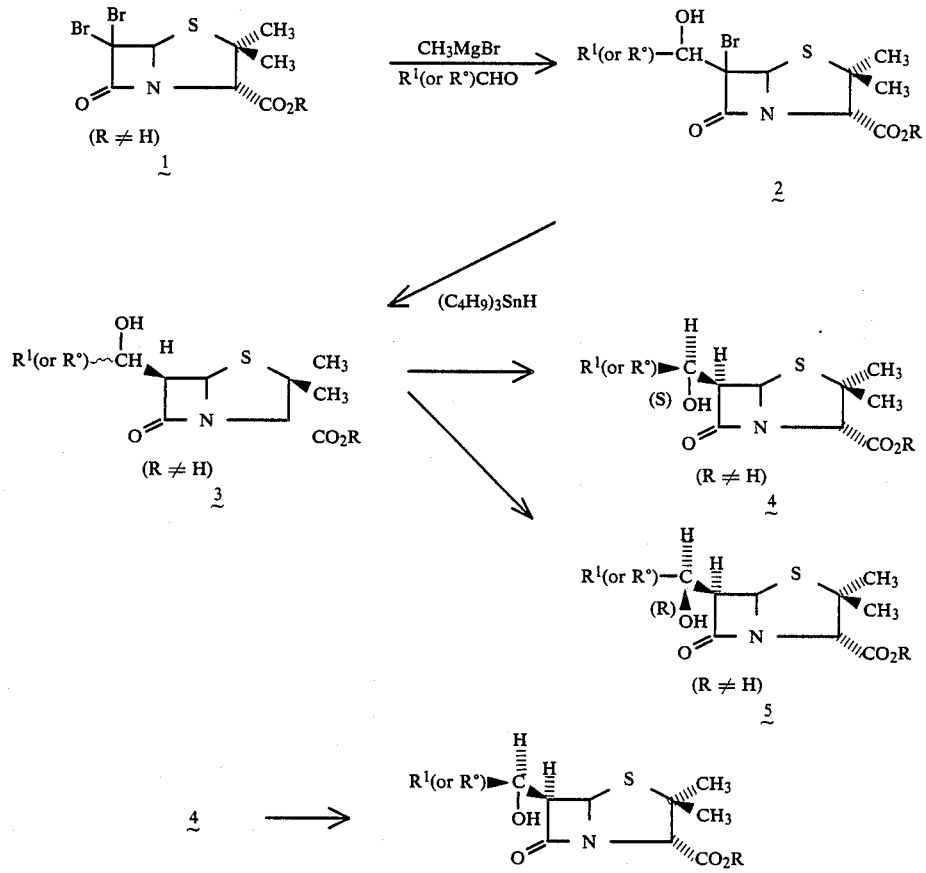

where $R^1$ and $R°$ are as previously defined.

In the first step of this sequence of reactions an ester of compound 1 a reaction inert solvent such as benzene, toluene xylene, pentane, tetrahydrofuran, methylene chloride, diethyl ether or mixtures thereof, is contacted at low temperatures with a Grignard reagent such as methyl magnesium bromide to form a magnesium penicillin intermediate. This is reacted with the appropriate aldehyde $R^1CHO$ or $R°CHO$, where $R^1$ and $R°$ are as previously defined, at about −78° C. The reaction, when complete, is quenched with acetic acid and water and the bromohydrin product 2 separated in a water immiscible solvent.

Reduction of 2 is carried out with an organotin hydride such as dihydrides, trialkyltin hydrides or triaryltin hydrides. The preferred reducing agent is tri-n-butyltin hydride.

The reaction employing said tin hydrides is ordinarily carried out in the presence of a reaction inert solvent.

In carrying out the hydrogenolysis employing organotin hydride reducing agents, equimolar amounts of bromohydrin and hydride is required by theory. In practice an excess of hydride is often employed to assure complete reaction.

The hydrogenolysis by organotin hydrides proceeds to substantial completion under the preferred conditions disclosed above without use of a catalyst. However, the reaction is expedited by means of a source of free radicals such as, e.g., ultraviolet light, or a catalytic amount of azobisisobutyronitrile or peroxides such as benzoyl peroxide. A catalytic amount of azobisisobutyronitrile is a preferred source of free radicals for this reaction.

Typically, the compound of formula 2 is dissolved in reaction inert solvent, the solution is maintained under an inert atmosphere, e.g., a nitrogen or argon atmosphere, and the appropriate amount of organotin hydride and, optionally, the source of free radicals, e.g., azobisisobutyronitrile, added and the resulting mixture stirred at a temperature within the preferred range of from about 0° C. up to the boiling point of the solvent. Reaction time at the reflux temperature is several hours and can be overnight for convenience sake.

The product 3 can be isolated by conventional methods known in the art. For example, the solvent can be removed and the residual product purified by chromatographing.

The use of the aforementioned tin hydrides provides products which are substituted at the 6-position in the beta-position; that is, the $R^1$—or $R°C(H)(OH)$—is in the beta configuration as attached to the 6-position of the penicillanate.

By the use of chromatography 3, which is a 6-beta compound can further be separated into two (4 and 5) isomers by virtue of the asymetric carbon of the carbinol attached at the 6-position. Of the 6-beta-(R) and 6-beta-(S) isomers available, the later is the preferred isomer and the compounds of the present invention.

As mentioned above, an especially preferred carboxy protecting group, R, is allyl. While this group can be removed by mild acid or alkaline hydrolyses procedures with satisfactory results, an especially preferred method for its removal employs a soluble palladium O complex, tetrakis (triphenylphosphine)palladium O as a catalyst, a method previously reported by Jeffrey and McCombie, J. Org. Chem., 47, 587–590 (1982). In a typical procedure the allyl ester in reaction inert solvent, e.g., ethylene dichloride, methylene chloride, chloroform, ethyl acetate, and a catalytic amount of tetrakis (triphenylphosphine)palladium, for example from about 1 to 5 mole percent based on the allyl ester, and an approximately equal weight of triphenylphosphine are combined under a nitrogen atmosphere. To this is added a sodium or potassium salt of 2-ethylhexanoate in an amount equimolar to the starting allyl ester and the resulting mixture is stirred at ambient temperature until precipitation of the desired salt is complete. Usually the reaction is substantially complete in from about two to twenty hours. The salt is then collected, e.g., by filtration.

The compounds of the invention, e.g., of formula 4 wherein R is an ester forming residue readily hydrolyzable in vivo can be prepared directly from the corresponding compound where R is hydrogen, sodium or potassium, by conventional esterification techniques. The specific method chosen will depend upon the precise structure of the ester forming residue, but an appropriate method will be readily selected by one skilled in the art. In the case where R is selected from 3-phthalidyl, 4-crotonolactonyl, gamma-butyrolacton-4-yl and groups of the formulae

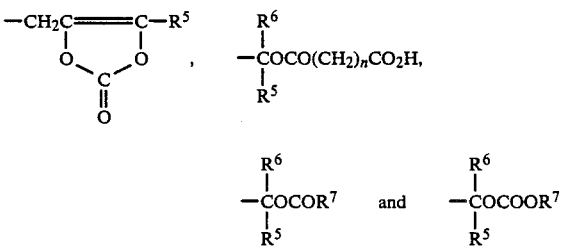

where n, $R^5$, $R^6$ and $R^7$ are as previously defined, they can be prepared by alkylation of the appropriate invention compound wherein R is hydrogen with a halide of the formula $R^bQ$, that is a 3-phthalidyl halide, a 4-crotonolactonyl halide, a gamma-butyrolacton-4-yl halide or a compound of the formula

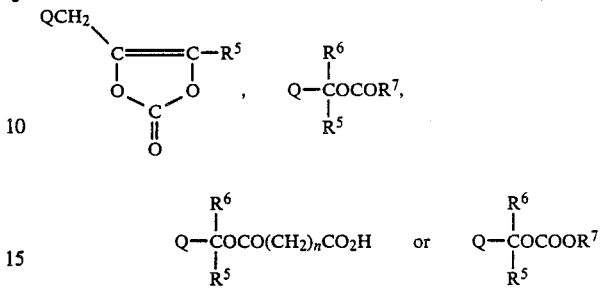

wherein Q is halo and $R^5$, $R^6$ and $R^7$ are as previously defined. The terms "halide" and "halo" are intended to mean derivatives of chlorine, bromine and iodine. The reaction is typically carried out by dissolving a salt of the compound of e.g., formula 4 wherein R is hydrogen in a suitable polar organic solvent, for example, N,N-dimethylformamide, and then adding about one molar equivalent of the appropriate halide ($R^bQ$). When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salts, tertiary amine salts, such as triethylamine, N-ethylpiperidine, N,N-dimethylaniline and N-methylmorpholine salts and quaternary ammonium salts, such as tetramethylammonium and tetrabutylammonium salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

Alternately, the readily hydrolyzable ester moiety can be incorporated into the structure of 1 and be carried through the sequence of steps, as previously described for R =allyl.

In addition, the ester

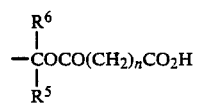

can also be prepared by hydrogenation of the corresponding benzyl ester

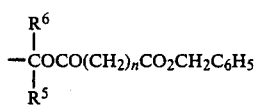

using hydrogen and a palladium-on-charcoal catalyst.

The starting aldehydes R¹CHO and R°CHO, wherein R¹ and R° are as previously defined, are either available from a commercial source or are prepared by methods known in the art, e.g., 1. Oxidation of the corresponding primary alcohol precursors employing e.g., oxidants such as potassium dichromate, chromic acid/pyridine, catalytic oxidation in the presence of noble metals, manganese dioxide or selenium dioxide.

2. Reaction of the corresponding methyl substituted aromatic hydrocarbon with e.g., selenium dioxide.

3. Reaction of an appropriate aromatic hydrocarbon precursor with n-butyl lithium and dimethylformamide or ethyl formate.

As indicated above, the compounds of the formula 4 wherein R is H, and salts thereof, show activity in vitro antibacterial tests. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing [Ericcson and Sherris, *Acta. Pathologica et Microbiologia Scandinav*, Supp. 217, Section B: 64–68 (1971)], and employs brain heart infusion (BHI) agar and the inocula replicating device. Ovenight growth tubes are diluted 100 fold for use as the standard inoculum (20,000–10,000 cells in approximately 0.002 ml are placed on the agar surface; 20 ml of BHI agar/dish). Twelve 2-fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of test compound or combination of compounds capable of producing complete inhibition of growth as judged by the naked eye.

As previously indicated, compounds of the present invention are potent antibacterial agents against a wide variety of microorganisms. Their potency against otherwise resistant organisms suggests that in addition to being antibacterial agents, they are inhibitors of beta-lactamase, the enzyme possessed by resistant microorganisms which inactivates beta-lactam antibiotics. This theory is corroborated by negligible increase in antibacterial activity by the combining of a compound of the present invention with a known beta-lactamase inhibitor against a specific microorganism.

Those compounds of the formula 4 where R is H, and salts thereof, are useful as industrial antimicrobials, for example in water treatment, slime control, paint preservation and wood preservation, as well as for topical application as disinfectants. In the case of use of these compounds for such an application, it is often convenient to admix the active ingredient with a non-toxic carrier, such as vegetable or mineral oil or an emollient cream. Similarly, they can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

More importantly, compounds of this invention can be employed in the treatment of bacterial infections in mammals, particularly man.

The compounds of the present invention wherein R and $R^9$ are hydrogen or the residue of an ester group readily hydrolyzable in vivo are antibacterial agents in vivo. In determining such activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, non-treated control mice). The test compound is administered at various dosage levels, p.o. or i.p., to groups of infected mice. At the end of the test, the activity is assessed by counting the number of survivors among treated animals at a given dose. Activity is expressed as the percentage of animals which survive at a given dose, or calculated as a $PD_{50}$ (dose which protects 50% of the animals from infection).

When used in vivo, these novel compounds can be administered orally or parenterally. When administered by the oral route, the daily dosage will be in the range of from about 10 to about 200 mg per kilogram of body weight. The daily parenteral dosage will be in the range of from about 10 to about 40 mg per kilogram of body weight. Vehicles suitable for parenteral injection may be either aqueous such as water, isotonic saline, isotonic dextrose, Ringer's solution or nonaqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The present invention is illustrated by the following examples. However, it should be understood that the invention is not limited to the specific details of these examples. Proton and $C^{13}$ nuclear magnetic resonance spectra were measured at 60, 250 or 300 MHz for solutions in deuterochloroform ($CDCl_3$), deuterium oxide ($D_2O$), perdeutero acetone ($CD_3COCD_3$) or perdeutero dimethyl sulfoxide (DMSO-$d_6$) and peak positions are expressed in parts per million (ppm) downfield from tetramethylsilane. The following abbreviations are used: s, singlet; d, doublet; dd, doublet of doublets; t, triplet; q, quartet; m, multiplet; b, broad.

EXAMPLE 1

6-beta-(2-[1-Vinylbenzimidazolyl]-(S)-hydroxy)methylpenicillanic Acid ($R=H$; $R^2=CH_2=CH-$)

A. 1-(2-hydroxyethyl)benzimidazole

A mixture of 35.4 g (0.3 mole) of benzimidazole and 26.4 g (0.3 mole) of ethylene carbonate was heated for 5 hours at 120° C. The cooled melt was treated with benzene (500 ml) and heated to reflux. The benzene was decanted from a yellow oil and cooled to give 18.48 g of product.

The yellow oil was seeded and allowed to stand for several days. Acetone was added to the semi-solid and the mixture filtered and the solids washed with chloroform. The washings were combined, concentrated to dryness and recrystallized from benzene, 10.47 g. The crop were combined to give 28.95 g of the desired product.

B. 1-(2-chloroethyl)benzimidazole

To a slurry of 30 g (0.185 mole) of 1-(2-hydroxyethyl)benzimidazole in 200 ml of methylene chloride was added dropwise 13.5 ml (0.185 mole) of thionyl chloride in 50 ml of the same solvent. The reaction mixture was stirred at room temperature for 4 hours. The reaction mixture was added to an equal volume of water and made basic (pH 8-9) by the addition of sodium bicarbonate. The organic phase was separated, dried over magnesium sulfate and evaporated to give 27.3 g of product.

C. 1-vinylbenzimidazole

To 3.61 g (20 mmoles) of 1-(2-chloroethyl)benzimidazole in 50 ml of tetrahydrofuran was added in portions 960 mg (20 mmoles) of 50% sodium hydride and the mixture allowed to stir for 3 hours. The solids were filtered, washed with tetrahydrofuran and the washings and filtrate evaporated to dryness. The residue was dissolved in acetonitrile, washed with hexane and the acetonitrile concentrated to give 2.77 g of product as a yellow oil.

D. 1-vinylbenzimidazole-2-carboxaldehyde

To a cold (−78° C.) solution of dry tetrahydrofuran (300 ml) containing 13.27 ml (94.6 mmoles) of diisopropylamine was added 37.86 ml of 2.5M solution of n-butyl lithium in hexane and the mixture stirred for 30 minutes. 1-Vinylbenzimidazole (13.6 g, 94.6 mmoles) in 50 ml of tetrahydrofuran was added and the mixture stirred for 30 minutes. Ethyl formate (8.4 ml, 104.1 mmoles) was then added and the reaction mixture stirred, allowing to warm to room temperature, overnight. Acetic acid (5.4 ml, 99.6 mmoles) was added and the reaction added to 500 ml of water and 300 ml of ethyl acetate. The organic layer was separated, the water layer extracted with additional ethyl acetate (2×100 ml), and the organic phases combined, dried over magnesium sulfate and concentrated to an oil, 17 g. The residue was purified by chromatographing on 700 g of silica gel using ethyl acetate-chloroform (1:9; v:v) as the eluent to give 6.7 g of product as a light brown solid.

E. Allyl 6-(2-[1-vinylbenzimidazolyl]-hydroxy)methyl-6-bromopenicillanate

To 100 ml of methylene chloride containing 3.1 g (7.98 mmoles) of allyl 6,6-dibromopenicillanate and cooled to −78° C., under nitrogen, was added 2.57 ml (7.98 mmoles) of a 2.5M solution of methyl magnesium bromide in ether, and the mixture stirred for 30 minutes. To the resulting reaction mixture was added 1.37 g (7.98 mmoles) of 1-vinyl-2-benzimidazole-2-carboxaldehyde in 20 ml of methylene chloride and the mixture allowed to stir for 2 hours. Acetic acid (0.45 ml, 7.98 mmoles) was then added and the mixture poured into 100 ml of water. The organic phase was separated, dried over magnesium sulfate and concentrated to give the product as a semi-solid.

F. Allyl 6-beta-(2-[1-vinylbenzimidazolyl]-(S) and (R)-hydroxy)methylpenicillanate To 50 ml of benzene containing the product of Example 1E (7.98 mmoles) was added 21.5 ml (79.8 mmoles) of tri-n-butyltin hydride and the mixture heated to reflux overnight. The reaction mixture was concentrated, the residue dissolved in acetonitrile and the organic solution washed (2×50 ml) with hexane. Removal of the acetonitrile gave the crude mixture of products as an oil, which was chromatographed on 150 g of silica gel using ethyl acetate-chloroform (1:9, v:v) as the eluent. The 6-beta-(R) isomer, 557 mg, was the less polar product, while the 6-beta-(S) isomer, 660 mg, was the more polar product.

The NMR spectrum for 6-beta-(S) (CDCl$_3$) showed absorption at 1.38 (s, 3H), 1.6 (s, 3H), 4.46 (s, 1H), 4.6 (d of d, J=Hz and 18 Hz, 1H), 4.64 (m, 2H), 5.2–5.5 (m, 4H), 5.54 (d, J=5 Hz, 1H), 5.86 (d, J=18 Hz, 1H), 5.8–6.0 (m, 1H), 7.2–7.4 (m, 3H), 7.48 (m, 1H) and 7.68 (m, 1H) ppm.

G. 6-beta-(2-[1-vinylbenzimidazolyl]-(S)-hydroxy)methylpenicillanic acid potassium salt To 660 mg (1.6 mmoles) of allyl 6-beta-(2-[1-vinylbenzimidazolyl]-(S)-hydroxy)methylpenicillanate in 10 ml of diethyl ether-ethyl acetate (1:1, v:v) was added 25 mg of triphenylphosphine, 25 mg of tetrakis (triphenylphosphine)palladium (0) and 3.2 ml of a 5M solution of potassium 2-ethylhexanoate (1.6 mmoles) in ethyl acetate and the mixture stirred for 30 minutes. The solids were filtered and washed with ether to give 600 mg of product as a yellow solid.

The NMR spectrum (D$_2$O) showed absorption at 1.34 (s, 3H), 1.54 (s, 3H), 4.24 (s, 1H), 4.44 (d of d, J=6 Hz and 14 Hz, 1H), 5.45 (m, 2H), 5.55 (d, J=6 Hz, 1H), 5.72 (d, J=14 Hz, 1H), 7.24 (m, 1H), 7.4 (m, 2H) and 7.7 (m, 2H) ppm.

EXAMPLE 2

Pivaloyloxymethyl 6-beta-(2-[1-vinylbenzimidazolyl]-(S)-hydroxy)methylpenicillanate ($R=(CH_3)_3CCO_2CH_2-$, $R^2=CH_2=CH-$)

Chloromethyl pivalate (0.2 ml, 1.4 mmoles) and 590 mg (1.43 mmoles) of potassium 6-beta-(2-[1-vinylbenzimidazolyl]-(S)-hydroxy)methylpenicillanate were added to 10 ml of dimethyl formamide and the resulting solution allowed to stir overnight. The reaction mixture was diluted with diethyl ether (100 ml) and the ether washed (3×50 ml) with water. The organic phase was dried over magnesium sulfate and evaporated to give 580 mg of a yellow oil which was chromatographed on 20 g of silica gel using ethyl acetate-chloroform (1:9, v:v). The fractions containing the product were combined and concentrated to give 424 mg of product.

The NMR spectrum (300 MHz, CDCl3) showed absorption at 1.16 (s, 9H), 1.36 (s, 3H), 1.58 (s, 3H), 4.44 (s, 1H), 4.59 (d of d, J=4 Hz and 12 Hz, 1H), 5.26–5.44 (m, 2H), 5.5 (d, J=4 Hz, 1H), 5.66 (d, J=12 Hz, 1H), 5.77 (AB$_q$, J$_{AB}$=4 Hz, 2H), 7.1–7.3 (m, 3H), 7.44 (m, 1H) and 7.62 (m, 1H) ppm.

EXAMPLE 3

Acetoxymethyl 6-beta-(2-[1-vinylbenzimidazolyl]-(S)-hydroxy)methylpenicillanate (R=CH3COCH2—; R2=CH2=CH—)

In a manner similar to Example 2, 200 mg of potassium 6-beta-(2-[1-vinylbenzimidazolyl]-(S)-hydroxy)-methylpenicillanate and 60 mg of chloroacetone gave 60 mg of the desired product as a white solid after chromatography on 25 g of silica gel.

The NMR (300 MHz-CDCl3) spectrum showed absorption at 1.44 (s, 3H), 1.66 (s, 3H), 2.15 (s, 3H), 4.28 (m, 1H), 4.52 (s, 1H), 4.63 (d of d, J=6 Hz and 12 Hz, 1H), 5.34–5.54 (m, 2H), 5.6 (d, J=6 Hz, 1H), 5.73 (d, J=12 Hz, 1H), 5.82 (AB$_q$, J$_{AB}$=6 Hz, 2H), 7.24–7.4 (m, 3H), 7.55 (d, 1H) and 7.73 (d, 1H) ppm.

EXAMPLE 4

5-Methyl-2-oxo-,1,3-dioxolen-4-ylmethyl-6-beta-(2-[1-vinylbenzimidazolyl]-(S)-hydroxy)methylpenicillanate

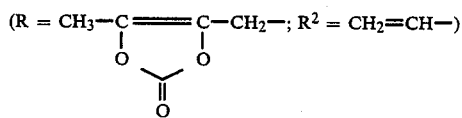

Starting with 411 mg (0.1 mmole) of potassium 6-beta-(2-[1-vinylbenzimidazolyl]-(S)-hydroxy)methylpenicillanate and 193 mg (0.1 mmole) of 4-bromomethyl-methyl-5-methyl-2-oxo-1,3-dioxolene and employing the procedure of Example 2, 280 mg of the desired product was isolated as a yellow solid.

The NMR spectrum (300 MHz, CDCl3) showed absorption at 1.32 (s, 3H), 1.6 (s, 3H), 2.15 (s, 3H), 4.44 (s, 1H), 4.52 (d of d, J=6 Hz and 10 Hz, 1H), 4.86 (AB$_q$, J=12 Hz, 2H), 5.3 (m, 1H), 5.41 (d, J=10 Hz, 1H), 5.53 (d, J=6 Hz, 1H), 5.64 (m, 1H), 7.16–7.3 (m, 3H), 7.48–7.56 (m, 1H) and 7.6–7.7 (m, 1H) ppm.

EXAMPLE 5

1-(Ethoxycarbonyloxy)-(R) and (S)-ethyl 6-beta-(2-[1-vinylbenzimidazolyl]-(S)-hydroxy)methylpenicillanate (R=C2H5OCOCH(CH3)—; R2=CH2=CH—)

Using the procedure of Example 2, 1.0 g (2.43 mmoles) of potassium 6-beta-(2-[1-vinylbenzimidazolyl](S)-hydroxy)methylpenicillanate and 0.33 ml (2.43 mmoles) of alpha-chlorodiethylcarbonate gave 496 mg of an orange oil. When chromatographed on 100 g of silica gel, there was obtained 162 mg of the ester having the (S) stereochemistry in the ester portion of the structure and 180 mg of the corresponding (R) isomer contaminated with some (S) isomer.

The NMR spectrum (300 MHz, CDCl3) of the (S) isomer showed absorption at 1.28 (t, 3H), 1.43 (s, 3H), 1.55 (d, 3H), 1.6 (s, 3H), 4.19 (q, 2H), 4.41 (s, 1H), 4.55 (d of d, J=4 Hz and 12 Hz, 1H), 5.33 (d, J=10 Hz, 1H), 5.43 (d, J=12 Hz), 5.56 (d, J=4 Hz, 1H), 5.68 (d, J=16 Hz, 1H), 6.75 (q, 1H), 7.2–7.4 (m, 3H), 7.5–7.6 (m, 1H) and 7.7–7.8 (m, 1H) ppm.

The NMR spectrum (300 MHz, CDCl3) of the (R) isomer showed absorption at 1.28 (t, 3H), 1.43 (s, 3H), 1.55 (d, 3H), 1.60 (s, 3H), 4.19 (q, 2H), 4.41 (s, 1H), 4.55 (dd, 1H), 5.33 (d, 1H), 5.43 (d, 1H), 5.56 (d, 1H), 5.68 (d, 1H), 6.75 (q, 1H), 7.2–7.4 (m, 3H), 7.5–7.6 (m, 1H) and 7.7–7.8 (m, 1H) ppm.

EXAMPLE 6

6-beta-(2-[1-Allylbenzimidazolyl]-(S)hydroxy)methylpenicillanic Acid (R=H; R2=CH2=CHCH2—)

A. 1-Allylbenzimidazole

To 11.8 g (0.1 mole) of benzimidazole in 50 ml of dimethylformamide was added portionwise 4.8 g (0.1 mole) of 50% sodium hydride. After stirring 30 minutes 8.65 ml (0.1 mole) of allyl bromide was added over a 20 minute period and the reaction mixture allowed to stir overnight.

The reaction mixture was poured into water acidified with 12N hydrochloric acid to pH 3. After extracting the acid with chloroform (2×25 ml), the aqueous layer was made basic (pH 10) with concentrated sodium hydroxide solution and extracted with chloroform (3×75 ml). The extracts were combined, dried over magnesium sulfate and concentrated to a pale yellow oil, 10 g.

B. 1-Allylbenzimidazole-2-carboxaldehyde

To a solution of 10 g (0.053 mole) of 1-allylbenzimidazole in 75 ml of tetrahydrofuran cooled to −78° C. was added 20.68 ml (0.053 mole) of 2.6M n-butyllithium in hexane over a period of 15 minutes. After 30 minutes of stirring 4.28 ml (0.053 mole) of ethyl formate was added and the reaction allowed to stir for one hour. Acetic acid (3.03 ml, 0.053 mole) was added, the cooling bath removed and the mixture allowed to warm to −20° C. The mixture was poured into water and the product extracted (3×100 ml) with ethyl acetate. The extracts were combined, dried over magnesium sulfate and concentrated to a brown oil which was chromatographed on 350 g of silica gel using ethyl acetate-chloroform as the eluent, 2.3 g.

C. Allyl 6-beta-(2-[1-allylbenzimidazolyl]hydroxymethyl-6-bromopenicillanate To 4.79 g (0.012 mole) of allyl 6,6-dibromopenicillanate in 100 ml of toluene cooled to −78° C. was added 3.87 ml (0.012 mole) of a 3.1M solution of methyl magnesium bromide in diethyl ether over a 5 minute period. After stirring for 30 minutes, 2.2 g (.012 mole) of 1-allylbenzimidazole-2-carboxaldehyde in 25 ml of toluene was added. After stirring one hour, 0.69 ml (0.012 mole) of acetic acid was added and the reaction mixture allowed to warm to 0° C. The mixture was poured into water and the product extracted with ethyl acetate. The extracts were combined, dried over sodium sulfate and concentrated to dryness. The unpurified material was employed in subsequent steps.

D. Allyl 6-beta-(2-[1-allylbenzimidazolyl]-(S) and (R)-hydroxy)penicillanate A mixture of 6.46 ml (0.024 mole) of tri-n-butyltin hydride and the product from Example 6C in 100 ml of benzene was heated to reflux for 6 hours and allowed to stir at room temperature overnight. The solvent was removed and the residue treated with acetonitrile-hexane. The acetonitrile layer was further washed with hexane and the solvent removed to give 5 g of product as a yellow oil. The residual oil was chromatographed on 200 g of silica gel using ethyl acetate-chloroform (2:8, v:v) as the eluent to give 522 mg of a less polar isomer, 6-beta-(R), and 625 mg of the more polar, desired isomer, 6-beta-(S).

The NMR spectrum (300 MHz, CDCl$_3$) of the 6-beta-(S) isomer showed absorption at 1.46 (s, 3H), 1.67 (s, 3H), 4.54 (s, 1H), 4.59 (d of d, J=4 Hz and 8 Hz, 1H), 4.69 (d, 2H), 5.08 (m, 2H), 5.2–5.48 (m, 4H), 5.46 (d, J=8 Hz, 1H), 5.68 (d, J=4 Hz, 1H), 5.84–6.08 (m, 2H), 7.18–7.42 (m, 3H) and 7.64–7.9 (m, 1H) ppm.

E. Potassium 6-beta-(2-[1-allylbenzimidazolyl]-(S)-hydroxy)penicillanate

A solution of 625 mg (1.46 mmoles) of allyl 6-beta(2-[1-allylbenzimidazolyl]-(S)-hydroxy)penicillanate, 50 mg of triphenylphosphine, 50 mg of tetrakis(triphenylphosphine)palladium and 2.92 ml (1.46 mmoles) of a 5M solution of potassium 2-ethylhexanoate in 2 ml ethyl acetate was allowed to stir for 45 minutes. The solids were filtered, 500 mg, and chromatographed on C$_{18}$ high performance liquid chromatography column using 20% acetonitrile in water, 109 mg.

The NMR spectrum (300 MHz, D$_2$O) showed absorption at 1.34 (s, 3H), 1.52 (s, 3H), 4.22 (s, 1H), 4.38 (d of d, 1H), 4.8–5.04 (m, 3H), 5.1–5.22 (m, 1H), 5.4 (d, 1H), 5.47 (d, 1H), 5.9–6.1 (m, 1H), 7.24–7.42 (m, 2H), 7.42–7.54 (m, 1H) and 7.64–7.76 (m, 1H) ppm.

EXAMPLE 7

6-beta-(2-[1-Hydroxyethylbenzimidazolyl]-(S)-hydroxy)methylpenicillanic Acid (R=H; R$^2$=HO(CH$_2$)$_2$—)

A. 1-t-butyldimethylsilyloxyethylbenzimidazole

A solution of 50 ml of tetrahydrofuran containing 2.5 g (15.4 mmoles) of 1-hydroxyethylbenzimidazole, 2.3 g (15.4 mmoles) of t-butyldimethylsilyl chloride and 1.0 g (15.4 mmoles) of imidazole was allowed to stir overnight at room temperature. The reaction mixture was poured into water and the product extracted with ethyl acetate (2×100 ml). The combined extracts were dried over magnesium sulfate and concentrated in vacuo to a colorless oil, 3.5 g. The intermediate was purified by chromatography on 100 g of silica gel using chloroform as the eluent, 3.11 g.

B. 1-t-butyldimethylsilyloxyethyl-benzimidazole-2-carboxaldehyde

To a solution of 3.11 g (11.3 mmoles) 1-t-butyldimethylsilyloxyethylbenzimidazole in 60 ml of dry tetrahydrofuran under nitrogen and cooled to −78° C. was added 4.35 ml (11.3 mmoles) of a 7.5M solution of n-butyl lithium in hexane, and stirred for 20 minutes. Ethyl formate ( 0.91 ml, 11.3 mmoles) was added and the reaction mixture stirred for one hour. Acetic acid (0.65 ml, 11.3 mmoles) was added to the reaction and the mixture poured into water (200 ml). The product was extracted with ethyl acetate and the combined extracts dried over magnesium sulfate and concentrated to give 3.42 g of a brown oil. The residue was chromatographed on 100 g of silica gel using chloroform as the eluent to give 2.32 g of product as an orange oil.

C. Allyl 6-beta-(2-[1-t-butyldimethylsilyloxyethylbenzimidazolyl]hydroxy)methyl-6-bromopenicillanate To 75 ml of toluene containing 3.05 g (7.63 mmoles) of allyl 6,6-dibromopenicillanate and cooled to −78° C. was added 2.46 ml (7.63 mmoles) of a 3.1M solution of methyl magnesium bromide in ether, and the mixture allowed to set for 15 minutes. 1-t-Butyldimethylsilyloxyethylbenzimidazole-2-carboxaldehyde (2.32 g, 7.63 mmoles) in 20 ml of toluene was added to the reaction and the mixture stirred for one hour. Acetic acid (0.436 ml, 7.63 mmoles) was then added, the mixture poured into 200 ml of water and the organic phase separated. The aqueous phase was further extracted with toluene and the organic extracts combined, dried over magnesium sulfate and concentrated to give the product as an orange glass.

D. Allyl 6-beta-(2-[1-t-butyldimethylsilyloxyethylbenzimidazolyl]-(S) and (R)-hydroxy)methylpenicillanate To the product from Example 7C in 50 ml of benzene was added 4.03 ml (15.27 mmoles) of tri-n-butyltin hydride and the reaction mixture heated to reflux for 6 hours. After standing at room temperature overnight, the solvent was removed and the residue was dissolved in acetonitrile. The acetonitrile solution was washed with hexane and was concentrated to give 4.5 g of crude product, which was chromatographed on 200 g of silica gel using 10% ethyl acetate chloroform as the eluent. The 6-beta-(R) isomer (566 mg) was isolated as the less polar material while the 6-beta-(S) isomer (865 mg) was the more polar product.

E. Allyl 6-beta-(2-[1-hydroxyethylbenzimidazolyl]-(S)-hydroxy)methylpenicillanate Allyl 6-beta-(2-[1-t-butyldimethylsilyloxyethylbenzimidazolyl]-(S)-hydroxy)methylpenicillanate (600 mg, 1.1 mmoles) and 0.126 ml (2.2 mmoles) of acetic acid were added to 6.6 ml (6.6 mmoles) of a 1M solution of tetrabutylammonium fluoride in tetrahydrofuran and the reaction mixture stirred overnight at room temperature under nitrogen. The reaction was diluted with ethyl acetate and the organic phase washed with water and a sodium bicarbonate solution. The organic phase was separated, dried over magnesium sulfate and concentrated. The residue was washed with hexane and dried, 484 mg.

The NMR spectrum (300 MHz, CDCl$_3$) showed absorption at 1.4 (s, 3H), 1.64 (s, 3H), 3.8–4.1 (m, 2H), 4.3–4.6 (m, 3H), 4.52 (s, 1H), 4.68 (d J=6 Hz, 2H), 5.1–5.5 (m, 3H), 5.62 (d, J=4 Hz, 1H), 5.86–6.04 (m, 1H), 7.1–7.4 (m, 3H) and 7.6–7.7 (m, 1H) ppm.

F. Potassium 6-beta-(2-[1-hydroxyethylbenzimidazolyl]-(S)-hydroxy)methylpenicillanate Following the general procedure of Example 1G, 84 mg (1.13 mmoles) of allyl 6-beta-(2-[1-hydroxyethylbenzimidazolyl]-(S)-hydroxy)methylpenicillanate, 20 mg of triphenylphosphine, 20 mg of tetrakis (triphenylphosphine)palladium (0) and 2.25 ml of a 0.5M solution of potassium 2-ethylhexanoate (1.13 mmoles) gave 484 mg of the desired product.

The NMR spectrum (300 MHz, D$_2$O) showed absorption at 1.42 (s, 3H), 1.62 (s, 3H), 4.0–4.1 (m, 2H), 4.32 (s, 1H), 4.4–4.7 (m, 3H), 5.5–5.6 (m, 2H), 7.36–7.5 (m, 2H), 7.68 (d, 1H) and 7.76 (d, 1H) ppm.

EXAMPLE 8

6-Beta-(2-[1-fluoroethylbenzimidazolyl]-(S)-hydroxy)methylpenicillanic Acid (R=H; R$^2$=FCH$_2$CH$_2$—)

A. 1-fluoroethylbenzimidazole

A solution of 3.24 g (0.02 mole) of 1-hydroxyethylbenzimidazole in 50 ml of methylene chloride was added to a solution of 2.44 ml (0.02 mole) of diethylaminosulfur trifluoride in 50 ml of methylene chloride cooled to −78° C. and under a nitrogen atmosphere. The reaction mixture was allowed to warm slowly to room temperature where it was stirred for 4 hours. The mixture was poured into water, the pH adjusted to 8 with aqueous sodium hydroxide solution and the organic layer separated and dried. Removal of the solvent gave 1.25 g of a brown oil which was chromatographed on 100 g of silica gel using 5% methanol chloroform as the eluent, 845 mg.

B. 1-fluoroethylbenzimidazole-2-carboxaldehyde

To a cold (−78° C.) solution of 30 ml of dry tetrahydrofuran containing 845 mg (5.15 mmoles) was added 1.98 ml (5.15 mmoles) of a 2.6M solution of n-butyl lithium in hexane, and the reaction mixture stirred for 20 minutes. Ethyl formate (0.416 ml, 5.15 mmoles) was added and the mixture was stirred for one hour. Acetic acid (0.295 ml, 5.15 mmoles) was then added and the reaction mixture poured into 100 ml of water. The product was extracted with ethyl acetate to give 850 mg of a yellow oil, which was chromatographed on 50 g of silica gel, 485 mg.

C. Allyl 6-(2-[1-fluoroethylbenzimidazolyl]hydroxy)methyl-6-bromopenicillanate To 977 mg (2.45 mmoles) of allyl 6,6-dibromopenicillanate in 30 ml of toluene cooled to −78° C. and under nitrogen was added 0.79 ml (2.45 mmoles) of a 3.1M solution of methyl magnesium bromide in ether and the mixture stirred for 15 minutes. 1-Fluoroethylbenzimidazole2-carboxaldehyde (470 mg, 2.45 mmoles) in 5 ml of toluene was added and the reaction mixture stirred for one hour. Acetic acid (0.14 ml, 2.45 mmoles) was added and the reaction poured into 100 ml of water. The toluene layer was separated, dried over magnesium sulfate and concentrated to give 1.3 g of the product as an orange oil.

D. Allyl 6-beta-(2-[1-fluoroethylbenzimidazolyl]-(S) and (R)-hydroxy)methylpenicillanate A solution of 10 ml of benzene containing 354 mg (0.69 mmole) of allyl 6-(2-[1-fluoroethylbenzimidazolyl]hydroxy)methyl-6-bromopenicillanate and 0.36 ml mmoles) of tri-n-butyltin hydride was stirred at reflux temperature for 3 hours. The benzene was removed and the residue taken up in acetonitrile. The acetonitrile layer was washed with hexane and concentrated to dryness. The residue was chromatographed on 100 g of silica gel using 10% ethyl acetate-chloroform as the eluent to give 105 mg of the desired isomer as a colorless oil.

The NMR spectrum (300 MHz, CDCl$_3$) showed absorption at 1.4 (s, 3H), 1.63 (s, 3H), 4.3–4.9 (m, 4H), 4.52 (s, 1H), 4.58 (d of d, J=6 Hz and 10 Hz, 1H), 4.68 (m, 2, 5.26–5.44 (m, 2H), 5.49 (d, J=10 Hz, 1H), 5.67 (d, J=6 Hz, 1H), 5.8–6.04 (m, 1H), 7.2–7.4 (m, 3H) and 7.63 (d, J=8 Hz, 1H) ppm.

E. Potassium 6-beta-(2-[1-fluoroethylbenzimidazolyl]-(S)-hydroxy)-methylpenicillanate Using the general procedure of Example 1G, 105 mg (0.24 mmole) of allyl 6-beta-(2-[1-fluoroethylbenzimidazolyl]-(S)-hydroxy)methylpenicillanate, 10 mg of triphenylphosphine, 10 mg of tetrakis (triphenylphosphine)palladium (O) and 0.5 ml (0.24 mmole) of a 0.5M potassium 2-ethylhexanoate solution in ethyl acetate gave 80 mg of the desired product.

The NMR spectrum (300 MHz, D$_2$O) showed absorption at 1.35 (s, 3H), 1.49 (s, 3H), 3.86 (s, 1H), 4.2 (d of d, J=4 Hz and 10 Hz, 1H), 4.5–4.94 (m, 4H), 5.24 (d, J=10 Hz, 1H), 5.39 (d, J=4 Hz, 1H), 7.18–7.34 (m, 2H) and 7.56–7.7 (m, 2H) ppm.

EXAMPLE 9

6-Beta-(2-[1-phenylimidazolyl]-(S)-hydroxy)methylpenicillanic Acid (R=H, R$^3$=C$_6$H$_5$)

A. 1-phenylimidazole-2-carboxaldehyde

To 50 ml of dry tetrahydrofuran containing 5.0 g (3.5 mmoles) of 1-phenylimidazole and cooled to −78° C. was added 13.8 ml (3.5 mmoles) of a 2.5M solution of n-butyllithium in hexane and the mixture stirred in the cold for one hour. Ethyl formate (2.8 ml, 3.5 mmoles) was then added and the mixture stirred for 80 minutes. Acetic acid (1.99 ml, 3.5 mmoles) was added and the cooling bath was removed. After stirring for 5 minutes the mixture was poured into water and the product extracted with ethyl acetate. The extracts were combined, dried over magnesium sulfate and concentrated to give 6.58 g of a pale yellow oil which solidified when triturated with a small amount of cold ether, 4.02 g.

B. Allyl 6-(2-[1-phenylimidazolyl]hydroxy)methyl-6-bromopenicillanate

To a solution of 6.95 g (0.017 mole) of allyl 6,6-dibromopenicillanate in 150 ml of methylene chloride chilled to −78° C. was added 6.2 ml (0.017 mole) of a 2.8M solution of methyl magnesium bromide in ether. After stirring for 30 minutes, 3.0 g (0.017 mole) of 1-phenylimidazole-2-carboxaldehyde in 20 ml of methylene was added and the reaction mixture stirred for 1.5 hours. Acetic acid (0.097 ml, 0.017 mole) was added, the reaction removed from the coolrng bath and stirring continued for 5 minutes. The mixture was poured into water and the organic phase separated and dried over magnesium sulfate. The solvent was then removed under vacuum and the residue used in subsequent reactions.

C. Allyl 6-beta-(2-[1-phenylimidazolyl]-(S) and (R)-hydroxy)methylpenicillanate To a solution of the product from Example 9B in 125 ml of dry tetrahydrofuran was added 9.14 ml (0.034 mole) of tri-n-butyltin hydride and the reaction mixture heated to reflux for 6 hours and then stirred at room temperature overnight. The solvent was removed and the residue dissolved in acetonitrile. The acetonitrile was washed with hexane (3×75 ml), separated and concentrated to a brown oil. The residue was chromatographed on 300 g of silica gel using 25% ethyl acetate in chloroform as the eluent to give 1.35 g of a product consisting of a mixture of isomers (R) and (S). On standing, one isomer (S) as a pale yellow solid precipitated and was filtered. The filtrate was triturated to give additional solids and the solids combined, 385 mg. The ether was removed from the filtrate to give the second isomer (R) as a yellow foam, 670 mg.

The NMR spectrum (300 MHz, CDCl$_3$) of the (S) isomer showed absorption at 1.32 (s, 3H), 1.34 (s, 3H), 4.32 (s, 1H), 4.40 (d of d, 1H), 4.58 (d, 1H), 4.92 (d, 1H), 5.18–5.4 (m, 3H), 5.77–5.94 (m, 1H), 7.0–7.22 (m, 2H) and 7.34–7.58 (m, 5H) ppm.

The NMR spectrum (300 MHz, CDCl$_3$) of the (R) isomer showed absorption at 1.38 (s, 3H), 1.43 (s, 3H), 4.25 (d of d, 1H), 4.36 (s, 1H), 4.5–4.70 (m, 2H), 5.07 (d, 1H), 5.18–5.38 (m, 2H), 5.58 (d, 1H), 5.78–5.98 (m, 1H), 6.98–7.18 (m, 2H) and 7.3–7.6 (m, 5H) ppm.

D. Potassium 6-beta-(2-[1-phenylimidazolyl]-(S)-hydroxy)methylpenicillanate

In a manner similar to the procedure of Example 1G, 385 mg (,0.93 mmole) of allyl 6-beta-(2-[1-phenylimidazolyl]-(S)-hydroxy]methylpenicillanate, 38 mg of triphenylphosphite, 38 mg tetrakis (triphenylphosphine)palladium (0) and 1.86 ml (0.93 mmole) of a 0.5M solution of potassium 2-ethylhexanoate in ethyl acetate gave 406 mg of product as a yellow solid.

The NMR spectrum (300 MHz, D$_2$O) showed absorption at 1.35 (s, 3H), 1.38 (s, 3H), 4.13 (s, 1H), 4.34 (d of d, 1H), 4.93 (d, 1H), 5.32 (d, 1H), 7.14 (s, 1H), 7,36 (s, 1H) and 7.44–7.76 (m, 5H) ppm.

EXAMPLE 10

6-beta-(2-[1-Phenylbenzimidazolyl]-(S) hydroxy)methylpenicillanic Acid (R=H, R$^2$=C$_6$H$_5$)

A. 1-phenyl-2-methylbenzimidazole

A solution of 10 g (0.054, mole) of N-phenyl-1,2phenylenediamine and 9.94 ml (0.054 mole) of triethylorthoacetate in 200 ml of ethanol was heated to reflux for 4 hours. The solvent was removed and the residue partitioned between chloroform and water. The organic layer was separated, dried and removed to give 11.99 g of product as an oil.

B. 1-phenylbenzimidazole-2-carboxaldehyde

To a solution of 5.0 g (0.024 mole) of 1-phenyl-2methylbenzimidazole in 200 ml of dioxane was added 2.66 g (0.024 mole) of selenium dioxide and the reaction heated to reflux for 7 hours. The solids were filtered and the filtrate concentrated to a brown oil. The residue was chromatographed on 200 g of silica gel using 7% ethyl acetate in chloroform as the eluent to give 2.68 g of purified product.

C. Allyl 6-(2-[1-phenylbenzimidazolyl]hydroxy)methyl-6-bromopenicillanate

To a chilled (−78° C.) solution of 4.81 g (0.012 mole) of allyl 6,6-dibromopenicillanate in 100 ml of methylene chloride was added 4.31 ml (0.012 mole) of a 2.8M solution of methyl magnesium bromide in ether and the reaction allowed to stir for 30 minutes. 1-Phenylbenzimidazole-2-carboxaldehyde (2.68 g, 0.012 mole) in 20 ml of methylene chloride was added and the reaction mixture stirred for one hour at −78° C. Acetic acid (0.686 ml, 0.012 mole) was added, the reaction stirred for 5 minutes and the mixture poured into water. The organic phase was separated, dried over sodium sulfate and magnesium sulfate and concentrated to give the intermediate product which was employed directly in subsequent reactions.

D. Allyl 6-beta-(2-[1-phenylbenzimidazolyl]-(S) and (R)-hydroxy)methylpenicillanate A solution of the residue from Example 10C and 6.46 ml (0.024 mole) of tri-n-butyltin hydride in 100 ml of tetrahydrofuran was heated to reflux for 5.5 hours and allowed to stir at room temperature for 48 hours. The solvent was removed and the residue dissolved in acetonitrile. The acetonitrile was washed with hexane (3×75 ml) and concentrated to a yellow oil, 5 g. The residue was chromatographed on 200 g of silica gel using 30% ethyl acetate in chloroform as the eluent to give 456 mg of the less polar (R) isomer, and 340 mg of the more polar (S) isomer.

The NMR spectrum (300 MHz, CDCl$_3$) of the (R) isomer showed absorption at 1.40 (s, 3H), 1.43 (s, 3H), 4.3 (d of d, 1H), 4.37 (s, 1H), 4.6 (d, 2H), 4.18–4.4 (m, 3H), 4.56 (d, 1H), 5.8–5.96 (m, 1H), 7.12–7.34 (m, 4H), 7.42–7.66 (m, 5H) and 7.8 (d, 1H) ppm.

The NMR spectrum (300 MHz, CDCl$_3$) of the (S) isomer showed absorption at 1.29 (s, 3H), 1.32 (s, 3H), 4.34 (s, 1H), 4.53–4.60 (m, 2H), 4.66 (d of d, 1H), 5.04–5.34 (m, 3H), 5.38 (d, 1H), 5.68–5.82 (m, 1H), 7.08–7.34 (m, 5H), 7.42–7.64 (m, 4H) and 7.80 (d, 1H) ppm.

E. Potassium 6-beta-(2-[1-phenylbenzimidazolyl] (S)-hydroxy)methylpenicillanate Employing the procedure of Example 1G, 340 mg of the (S) isomer of Example 10D, 1.46 ml (0.073 mmole) of a 5M solution of potassium 2-ethylhexanoate in ethyl acetate, 34 mg of triphenylphosphine and 34 mg of tetrakis (triphenylphosphine)palladium (0) in 2 ml of ethyl acetate gave 94 mg of the desired product.

The NMR spectrum (300 MHz, D$_2$O) showed absorption at 1.33 (s, 6H), 4.14 (s, 1H), 4.42 (d of d, 1H), 5.07 (d, 1H), 5.4 (d, 1H), 7.26–7.43 (m, 3H), 7.52–7.72 (m, 6H) and 7.76 (d, 1H) ppm.

EXAMPLE 11

6-beta-(2-[1-Vinylimidazolyl]-(S)-hydroxy)methylpenicillanic Acid (R=H; R$^3$=CH$_2$=CH—)

A. 1-vinylimidazole-2-carboxaldehyde

To a cold (−78° C.) solution of 6.55 ml (0.047 mole) of diisopropylamine in 125 ml of tetrahydrofuran was added 16.99 ml (,042 mole) of a 2.5M solution of n-butyl lithium over a period of 15 minutes and the resulting reaction allowed to stir for 30 minutes. 1-Vinylimidazole (3.85 ml 0.042 mole) was added over a 10 minute period and the mixture stirred for one hour. Ethyl formate (3.43 ml, 0.042 mole) was then added over 5 minutes and the mixture stirred for one hour and was then poured into a saturated ammonium chloride solution. The product was extracted with ethyl acetate, and the extracts combined, dried over magnesium sulfate and concentrated to an orange oil. The residue was chromatographed on 200 g of silica gel using 10% ethyl acetate in chloroform to give 2.23 g of the product as a crystalline material.

B. Allyl 6-(2-[1-vinylimidazolyl]hydroxy)methyl-6-bromopenicillanate

Following the general procedure of Example 1E, 2.23 g (0.018 mole) of 1-vinylimidazole-2-carboxaldehyde, 7.29 g (0.018 mole) of allyl 6,6-dibromopenicillanate gave the desired intermediate product on work-up.

C. Allyl 6-beta-(2-[1-vinylimidazolyl]-(S) and (R)-hydroxy)methylpenicillanate Employing the procedure of Example 1F and a reflux period of one hour, the product from Example 11B and 24.2 ml of tri-n-butyltin hydride in 125 ml of benzene gave 1.97 g of the (S) isomer contaminated with the (R) isomer.

D. Potassium 6-beta-(2-[1-vinylimidazolyl]-(S)-hydroxy)methylpenicillanate

Using the procedure of Example 1G, 1.97 g (0.52 mmole) of the product from Example 11c, 180 mg of triphenylphosphine, 10.84 ml (0.52 mmole) of 0.5M solution of potassium 2-ethylhexanoate in ethyl acetate and 180 mg of tetrakis (triphenylphosphine)palladium (0) in 5 ml of ethyl acetate gave, after chromatographing, 1.06 g of the desired (S) isomer and 322 mg of the (R) isomer.

The NMR spectrum (300 MHz, $D_2O$) of the (S) isomer showed absorption at 1.39 (s, 3H), 1.57 (s, 3H), 4.20 (s, 1H), 4.28 (d of d, 1H), 5.12 (d, 1H), 5.27 (d, 1H), 5.35 (d, 1H), 5.48 (d, 1H), 6.98 (s, 1H), 7.16 (d of d, 1H) and 7.47 (s, 1H) ppm.

EXAMPLE 12

6-beta-(2-[1-cyclopropylbenzimidazolyl]-(S)-hydroxy)-methylpenicillanic Acid

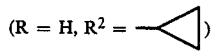

($R = H, R^2 = $ cyclopropyl)

A. N-cyclopropyl-2-nitroaniline

1-Chloro-2-nitroaniline (13 g, 0.082 mole) and 17.15 ml of cyclopropylamine were heated together at reflux temperature for 24 hours, cooled and poured into ethyl acetate. The organic solution was washed with a saturated brine solution (3×100 ml), dried with magnesium sulfate and concentrated to dryness. The residue was chromatographed on silica gel using 60% hexane in chloroform to give 2.04 g of the desired intermediate.

B. N-cyclopropyl-1,2-phenylenediamine

A suspension of 2.85 g of N-cyclopropyl-2-nitrobenzene and 172 mg of 10% palladium-on-charcoal in 50 ml of ethanol was shaken in a hydrogen atmosphere at an initial press of 40 psi for 2 hours. The reaction was filtered and the filtrate concentrated in vacuo to give the product as a dark gum.

C. 1-cyclopropyl-2-methylbenzimidazole

A solution of 1.71 g (0.0115 mole) of N-cyclopropyl-1,2-phenylenediamine and 2.12 ml (0.0115 mole) of triethylorthoacetate in 50 ml of ethyl acetate was heated to reflux for 2 hours. The solvent was removed and the residue partitioned between chloroform and water. The organic phase was separated, dried over sodium sulfate and concentrated to give 1.87 g of a brown oil.

D. 1-cyclopropylbenzimidazole-2-carboxaldehyde

Selenium dioxide (1.2 g, 0.011 mole) was added to 60 ml of dioxane containing 1.87 g .(0.011 mole) of 1-cyclopropyl-2-methylbenzimidazole and the reaction heated to reflux for 2.5 hours. The reaction was filtered and the filtrate concentrated to a dark oil, 3.0 g. Chromatographing of the residue on silica gel gave 1.18 g of the desired compound.

E. Allyl 6-(2-[1-cyclopropylbenzimidazolyl]hydroxy)methyl-6-bromopenicillanate Following the procedure of Example 1E, 2.53 g (6.33 mmoles) of the aldehyde of Example 12D, 2.04 ml (6.33 mmoles) of a 3.1M solution of methyl magnesium bromide in ether and 1.18 g of allyl 6,6-dibromopenicillanate in 60 ml of methylene chloride gave, on workup, the desired product. F. Allyl 6-beta-(2-[1-cyclopropylbenzimidazolyl](S) and (R)-hydroxy)methylpenicillanate Using the procedure of Example 1F, the product from Example 12E and 3.61 ml of tri-n-butyltin hydride in 75 ml of tetrahydrofuran gave, after chromatographing the crude product on silica gel, 320 mg of the desired (S) isomer and 140 mg of the (R) isomer.

The NMR spectrum (300 MHz, $CDCl_3$) of the (S) isomer showed absorption at 1.0–1.58 (m, 4H), 1.4 (s, 3H), 1.69 (s, 3H), 3.28–3.44 (m, 1H), 4.52 (s, 1H), 4.62 (d, 2H), 4.68 (d of d, 1H), 5.2–5.42 (m, 2H), 5.46 (d, 1H), 5.62 (d, 1H), 5.8–5.96 (m, 1H), 7.10–7.30 (m, 2H), 7.36–7.50 (m, 1H) and 7.6–7.74 (m, 1H) ppm.

G. Potassium 6-beta-(2-[1-cyclopropylbenzimidazolyl]-(S)-hydroxy)methylpenicillanate The procedure of Example 1G is repeated, using 1.62 ml (0.081 mmole) of a 0.5M solution of potassium 2-ethylhexanoate in ethyl acetate, 30 mg of triphenylphosphine, 30 mg of tetrakis (triphenylphosphine)palladium (O) and 320 mg of the product from Example 12F, to give 230 mg of the desired product.

The NMR spectrum ($D_2O$, 300 MHz) showed absorption at 1.06–1.46 (m, 4H), 1.36 (s, 3H), 1.60 (s, 3H), 3.38–3.48 (m, 1H), 4.27 (s, 1H), 4.41 (d of d, 1H), 5.40 (d, 1H), 5.66 (d, 1H), 7.25–7.46 (m, 2H) and 7.60–7.80 (m, 2H) ppm.

EXAMPLE 13

6-beta-(2-[1-Methoxybenzimidazolyl]-(S)-hydroxy)-methylpenicillanic Acid ($R=H; R^2=CH_3$—)

A. 1-methoxy-2-methylbenzimidazole

To a solution of 7.8 g (0.53 mole) of 2-methylbenzimidazole N-oxide [Chem. Pharm. Bull., 11, 1375 (1963)] in 50 ml of dimethylformamide was added 2.53 g (0.053 mole) of 50% sodium hydride in oil over a period of 5 minutes. After stirring 15 minutes, 3.33 ml (0.053 mole) of methyl iodide was added over a 15-minute period and the reaction mixture allowed to stir at room temperature for 3 hours. The reaction was poured into water, the pH adjusted to 2 with 12N hydrochloric acid and the impurities extracted with ethyl acetate. The pH was adjusted to 12 with 6N sodium hydroxide solution and the product extracted with ethyl acetate (3×100 ml). The extracts were combined, dried over magnesium sulfate and evaporated under a nitrogen stream.

The residue was triturated with diethyl ether and the filtered solids chromatographed on 60 g of silica gel using 30% ethyl acetate-chloroform, 300 mg.

B. 1-methoxybenzimidazole-2-carboxaldehyde

By a procedure similar to that of Example 10B, 1.91 g of the product of Example 13A and 1.3 g of selenium dioxide in 30 ml of dioxane gave 490 mg of the desired product.

C. allyl 6-(2-[1-methoxybenzimidazolyl]hydroxy)methyl-6-bromopenicillanate

Following the procedure of Example 1E 490 mg of the aldehyde of Example 13B, 0.993 ml of 2.8M methyl magnesium bromide in ether and 1.11 g of allyl 6,6-dibromopenicillanate in 50 ml of methylene chloride gave a quantitative yield of the desired product.

D. allyl 6-beta-(2-[1-methoxybenzimidazolyl]-(S) and (R)-hydroxy)methyl penicillanate Using the procedure of Example 1F, the product of Example 13C and 1.51 ml of tri-n-butyltin hydride in 25 ml of tetrahydrofuran gave, after workup, 150 mg of the (S) isomer and 200 mg of an (S) and (R) mixture in a ratio of 4:3, respectively.

The NMR spectrum (300 MHz, CDCl$_3$) of the (S) isomer showed absorption at 1.36 (s, 3H), 1.61 (s, 3H), 3.78 (s, 3H), 4.45 (s, 1H), 4.52 (d of d, 1H), 4.6 (d, 2H), 5.16–5.46 (m, 3H), 5.53 (d, 1H), 5.78–5.96 (m, 1H), 7.1–7.3 (m, 3H) and 7.56–7.68 (m, 1H) ppm.

E. potassium 6-beta-(2-[1-methoxybenzimidazolyl](S)-hydroxy)methylpenicillanate The procedure of Example 1G is employed using 0.78 ml of 0.5M potassium 2-ethylhexanoate in ethyl acetate, 15 mg of triphenylphosphine, 15 mg of tetrakis (triphenylphosphine)palladium (O) and 150 mg of the product of Example 13D to give 64 mg of the desired product.

The NMR spectrum (300 MHz, D$_2$O) showed absorption at 1.4 (s, 3H), 1.62 (s, 3H), 3.92 (s, 3H), 4.28 (s, 1H), 4.43 (d of d, 1H), 5.48–5.54 (m, 2H), 7.24–7.48 (m, 2H), 7.52–7.64 (m, 1H) and 7.64–7.76 (m, 1H) ppm.

EXAMPLE 14

Starting with the appropriate aldehyde and allyl 6,6-dibromopenicillanate and employing the procedures of Examples 1E and 1F the following (S) isomers were prepared.

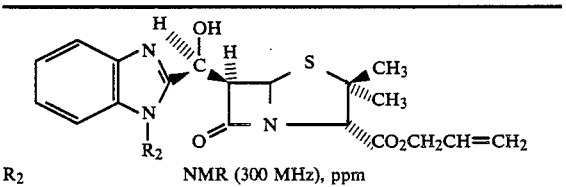

| R$_2$ | NMR (300 MHz), ppm |
|---|---|
| —CH$_2$OCH$_3$ | (CDCl$_3$) 1.4 (s, 3H), 1.62 (s, 3H), 3.32 (s, 3H), 4.52 (s, 1H), 4.60 (d of d, 1H), 4.67 (d, 2H), 5.26–5.46 (m, 2H), 5.46–5.7 (m, 3H), 5.74 (d, 1H), 5.86–6.04 (m, 1H), 7.22–7.37 (m, 2H), 7.37–7.52 (m, 1H) and 7.64–7.82 (m, 1H); |
| —CH$_2$CH$_2$OCH$_3$ | (CDCl$_3$) 1.38 (s, 3H), 1.63 (s, 3H), 3.28 (s, 3H), 3.66–3.72 (m, 2H), 4.26–4.62 (m, 3H), 4.48 (s, 1H), 4.6 (d, 2H), 5.2–5.44 (m, 3H), 5.58 (d, J=4 Hz, 1H), 5.8–6.0 (m, 1H), 7.14–7.3 (m, 3H) and 7.62–7.66 (d, 1H); |
| —CH$_2$F | 1.36 (s, 3H), 1.59 (s, 3H), 2.82 (d, 1H), 4.41 (d of d, 1H), 4.42 (s, 1H), 4.46 (d, 2H), 5.36 (m, 2H), 5.56 (d, 1H), 5.58 (d, 1H), 5.78–5.94 (m, 1H), 6.29 (2 × AB$_q$, ABX J$_{AB}$=3.5 Hz ½(J$_{AX}$-J$_{BX}$)=18 Hz, 2H), 7.18–7.42 (m, 3H) and 7.6–7.74 (m, 1H); |
| —CH$_2$-⟨thiophene⟩ | (CDCl$_3$) 1.3 (s, 3H), 1.45 (s, 3H), 4.4 (s, 1H), 4.54 (d of d, 1H), 4.62 (d, 2H), 5.2–5.8 (m, 6H), 5.8–6.0 (m, 1H), 6.84–6.92 (m, 1H), 6.94–6.98 (m, 1H), 7.14–7.3 (m, 4H) and 7.56–7.66 (m, 1H); |

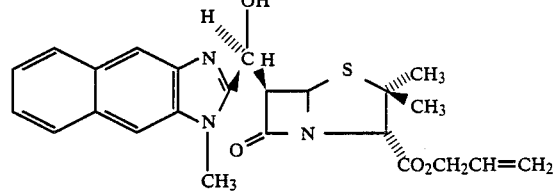

(CDCl$_3$) 1.34 (s, 3H), 1.6 (s, 3H), 3.74 (s, 3H), 4.46 (s, 1H), 4.6 (m, 3H), 5.2–5.4 (m, 2H), 5.42 (d, J=12 Hz, 1H), 5.38 (d, J=6 Hz, 1H), 5.8–6.01 (m, 1H), 7.2 (m, 1H), 7.25–7.5 (m, 2H), 7.74 (d, 1H), 7.84 (d, 1H) and 8.0 (s, 1H);

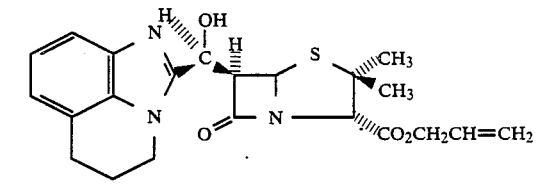

(CDCl$_3$) 1.34 (s, 3H), 1.59 (s, 3H), 2.0–2.1 (m, 2H), 2.64–2.86 (m, 2H), 4.1–4.2 (m, 2H), 4.44 (s, 1H), 4.52 (d of d, J=4 Hz, 10 Hz, 1H), 4.59 (d, 2H), 5.2–5.34 (m, 2H), 5.34 (d, J=10 Hz, 1H), 5.46 (d, J=4 Hz, 1H), 6.87 (d, 1H), 7.04 (t, 1H) and 7.39 (d, 1H);

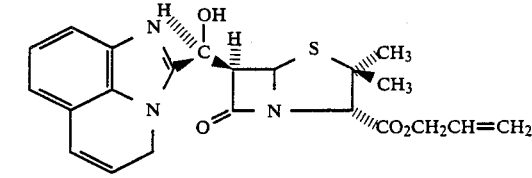

(CDCl$_3$) 1.37 (s, 3H), 1.61 (s, 3H), 4.45 (s, 1H), 4.45 (d of d, J=5 Hz, 10 Hz, 1H), 4.61 (d, 2H), 5.0–5.4 (m, 5H), 5.53 (d, J=5 Hz, 1H), 5.7–5.8 (m, 1H), 5.8–5.9 (m, 1H), 6.42–6.5 (m, 1H), 6.75 (d, 1H), 6.97 (t, 1H) and 7.34 (d, 1H);

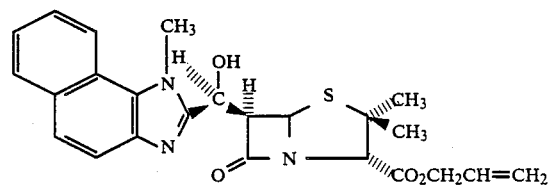

(CDCl$_3$) 1.6 (s, 3H), 4.15 (s, 3H), 4.47 (s, 1H), 4.6 (d, 1H), 4.61 (d of d, 1H), 5.18–5.38 (m, 2H), 5.42 (d, 1H), 5.54 (d, 1H), 5.78–5.94 (m, 1H), 7.26–7.4 (m, 2H), 7.5 (d, 1H), 7.64 (d, 1H), 7.75 (d, 1H) and 8.03 (d, 1H);

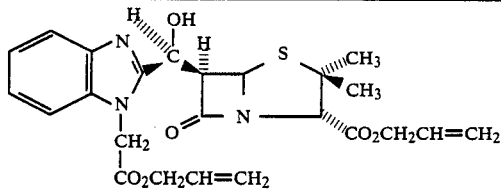

(CDCl₃) 1.44 (s, 3H), 1.64 (s, 3H), 4.4 (d of d, 1H), 4.48 (s, 1H), 4.98–5.42 (m, 6H), 5.49 (d, 1H), 5.64 (d, 1H), 5.74–6.0 (m, 2H), 7.14–7.36 (m, 3H) and 7.62–7.78 (m, 1H);

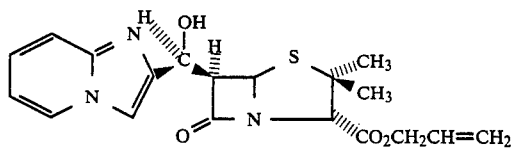

(CDCl₃) 1.34 (s, 3H), 1.6 (s, 3H), 4.53 (d of d, 1H), 4.4 (s, 1H), 4.55 (d, 2H), 5.14–5.36 (m, 4H), 5.74–5.9 (m, 1H), 6.64–6.76 (m, 1H), 7.04–7.15 (m, 1H), 7.42–7.60 (m, 2H) and 7.94–8.02 (m, 1H);

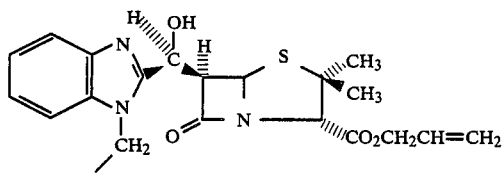

(CDCl₃) 1.63 (s, 3H), 1.6 (s, 3H), 2.04 (s, 3H), 4.45 (s, 1H), 4.5 (d of d, 1H), 4.6 (d, 2H), 5.09–5.5 (m, 4H), 5.54 (d, 1H), 5.62 (d, 1H), 5.78–5.96 (m, 1H), 7.12–7.3 (m, 2H), 7.3–7.48 (m, 1H) and 7.48–7.8 (m, 1H);

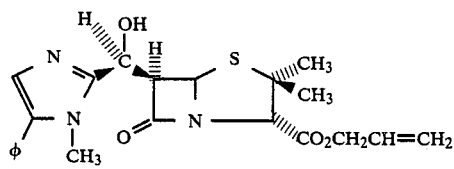

(CDCl₃) 1.39 (s, 3H), 1.62 (s, 3H), 3.64 (s, 3H), 4.41 (d of d, 1H), 4.42 (s, 1H), 4.58 (d, 2H), 5.16–5.38 (m, 3H), 5.5 (d, 1H), 5.75–5.84 (m, 1H), 6.91 (s, 1H) and 7.24–7.46 (m, 5H);

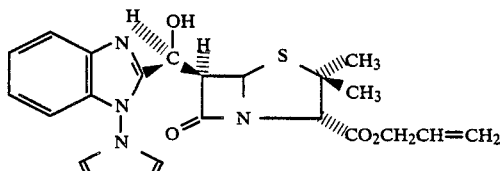

(CDCl₃) 1.36 (s, 3H), 1.48 (s, 3H), 4.38 (s, 1H), 4.49 (d of d, 1H), 4.6 (d, 2H), 5–5.12 (m, 1H), 5.2–5.4 (m, 2H), 5.48 (d, 1H), 5.76–5.96 (m, 1H), 6.31–6.40 (m, 2H), 6.9–7.14 (m, 2H), 7.20–7.38 (m, 3H) and 7.7–7.92 (m, 1H);

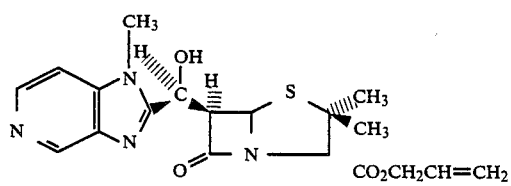

(CDCl₃) 1.38 (s, 0.75 × 3H), 1.48 (s, 0.25 × 3H), 1.60 (s, 0.75 × 3H), 1.86 (s, 0.25 × 3H), 3.81 (s, 0.25 × 3H), 3.86 (s, 0.75 × 3H), 4.45 (m, 2H), 4.62 (m, 2H), 5.2–5.4 (m, 4H), 5.6 (m, 1H), 7.2 (m, 1H), 8.3 (d, J=5 Hz, 1H) and 8.9 (s, 1H) ppm.

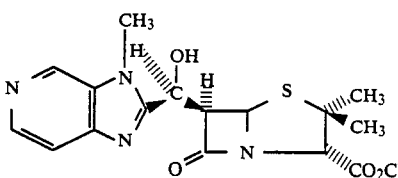

(CDCl₃) mixture comprising
45% 6-beta, 8S
22% 6-beta, 8R and
33% 6-alpha.

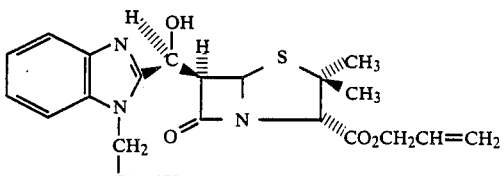

(CDCl₃) 1.36 (s, 3H), 1.6 (s, 3H), 2.33 (t, 1H), 4.46 (s, 1H), 4.47 (dd, J=4.5 Hz, 10 Hz, 1H), 4.61 (d, 2H), 5.05 (ab q, J=18 Hz, 2H), 5.23–5.37 (m, 2H), 5.53 (d, J=10 Hz, 1H), 5.58 (d, J=4.5 Hz, 1H), 5.9–6.0 (m, 1H), 7.2–7.26 (m, 2H), 7.34–7.37 (m, 1H) and 7.60–7.64 (m, 1H) ppm.

EXAMPLE 15

Starting with the appropriate allyl ester and employing the procedure of Example 1G, the following products were prepared.

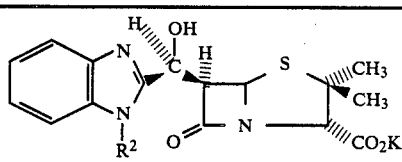

| R² | NMR (300 MHz), ppm |
|---|---|
| CH₂C≡CH | (D₂O) 1.42 (s, 3H), 1.63 (s, 3H), 2.83 (m, 1H), 4.31 (s, 1H), 4.46 (dd, J=4 Hz, 11 Hz, 1H), 5.23 (s, 2H), 5.55 (d, J=4 Hz, 1H), 5.6 (d, J=11 Hz, 1H), 7.36–7.5 (m, 2H) and 7.68–7.8 (m, 2H); |
| —CH₂OCH₃ | (D₂O) 1.34 (s, 3H), 1.53 (s, 3H), 3.28 (s, 3H), 4.22 (s, 1H), 4.37 (d of d, 1H), 5.4–5.54 (m, 2H), 5.54–5.76 (m, 2H), 7.22–7.44 (m, 2H) and 7.44–7.80 (m, 2H); |
| —CH₂CH₂OCH₃ | (D₂O) 1.36 (s, 3H), 1.57 (s, 3H), 3.23 (s, 3H), 3.8–3.9 (m, 2H), 4.24 (s, 1H), 4.4 (d of d, J=4 Hz, 10 Hz, 1H), 4.46–4.6 (m, 2H), 5.46 (d, J=10 Hz, 1H), 5.5 (d, J=4 Hz, 1H), 7.3–7.44 (m, 2H), 7.58 (d, 1H) and 7.68 (d, 1H); |
| —CH₂—[thiophene] | (D₂O) 1.26 (s, 3H), 1.39 (s, 3H), 4.2 (s, 1H), 4.41 (d of d, J=4 Hz, 10 Hz, 1H), 5.46 (d, J=10 Hz, 1H), 5.48 (d, J=4 Hz, 1H), 5.5–5.7 (m, 2H), 6.8–6.9 (m, 1H), 6.96–7.04 (m, 1H), 7.1–7.3 (m, 3H), 7.5–7.6 (m, 1H) and 7.6–7.7 (m, 1H); |
| —CH₂F | 1.42 (s, 3H), 1.62 (s, 3H), 4.29 (s, 1H), 4.44 (d of d, 1H), 5.46–5.68 (m, 2H), 6.47 (d, J_{AB}=17 Hz, 2H), 7.35–7.6 (m, 2H) and 7.62–7.84 (m, 2H); |

-continued

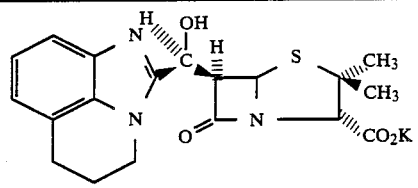

(D$_2$O) 1.39 (s, 3H), 1.61 (s, 3H), 2.22 (m, 2H), 2.98 (m, 2H), 4.26 (s, 1H), 4.2–4.3 (m, 2H), 4.4 (d of d, J=4 Hz, 10 Hz, 1H), 5.41 (d, J=4 Hz, 1H), 5.44 (d, J=10 Hz, 1H), 7.14 (d, 1H), 7.26 (t, 1H) and 7.49 (d, 1H);

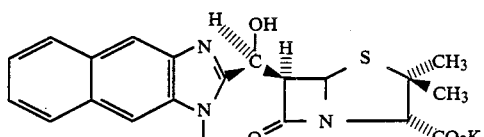

(D$_2$O) 1.34 (s, 3H), 1.58 (s, 3H), 3.82 (s, 3H), 4.24 (s, 1H), 4.43 (d of d, J=6 Hz, 12 Hz, 1H), 5.46 (d, J=12 Hz, 1H), 5.49 (d, J=6 Hz, 1H), 7.3–7.5 (m, 2H), 7.7 (s, 1H), 7.8–7.96 (m, 2H) and 8.0 (s, 1H);

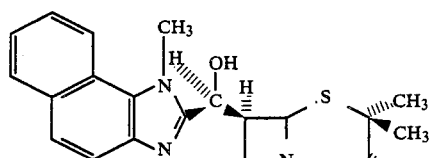

(D$_2$O) 1.31 (s, 3H), 1.43 (s, 3H), 3.86 (s, 3H), 4.25 (s, 1H), 4.45 (d of d, 1H), 5.34–5.48 (m, 2H), 7.04–7.26 (m, 3H), 7.36–7.54 (m, 2H) and 7.66–7.8 (m, 1H);

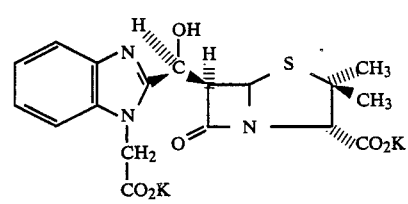

(D$_2$O) 1.45 (s, 3H), 1.65 (s, 3H), 4.31 (s, 1H), 4.46 (d of d, 1H), 4.97 (s, 2H), 5.46 (d, 1H), 5.53 (d, 1H), 7.36–7.58 (m, 3H) and 7.6–7.82 (m, 1H);

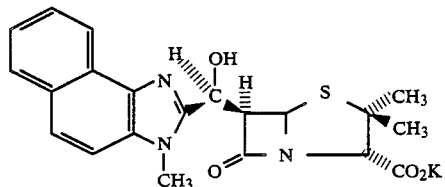

(D$_2$O) 1.3 (s, 3H), 1.54 (s, 3H), 3.76 (s, 3H), 4.23 (s, 1H), 4.52 (d of d, 1H), 5.42 (m, 2H), 7.26 (d, 1H), 7.36–7.54 (m, 2H), 7.54–7.64 (m, 1H), 7.79 (d, 1H) and 8.38 (d, 1H);

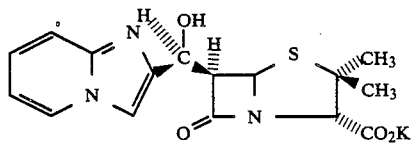

(D$_2$O) 1.39 (s, 3H), 1.62 (s, 3H), 4.21 (s, 1H), 4.27 (d of d, 1H), 5.2–5.4 (m, 2H), 6.85–7.0 (m, 1H), 7.38–7.42 (m, 1H), 7.43–7.76 (m, 1H), 7.76–7.93 (m, 1H) and 8.26–8.4 (m, 1H);

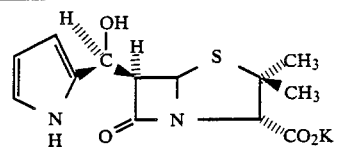

(D$_2$O) 1.45 (s, 3H), 1.65 (s, 3H), 4.17 (d of d, 1H), 4.22 (s, 1H), 5.12 (d, 1H), 5.29 (d, 1H), 6.12–6.28 (m, 2H) and 6.89 (s, 1H);

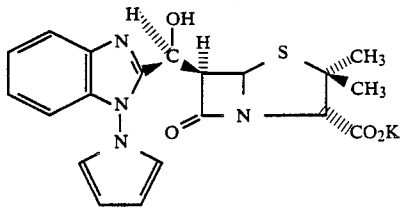

(D$_2$O) 1.41 (s, 3H), 1.56 (s, 3H), 4.22 (s, 1H), 4.3 (d of d, 1H), 5.04 (d, 1H), 5.48 (d, 1H), 6.46 (s, 2H), 7.12–7.3 (m, 3H), 7.46–7.48 (m, 2H) and 7.74–7.84 (m, 1H);

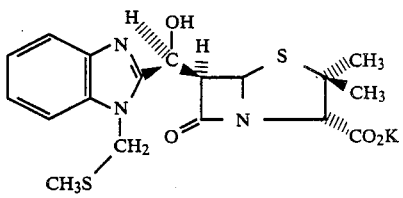

(D$_2$O) 1.42 (s, 3H), 1.64 (s, 3H), 2.1 (s, 3H), 4.29 (s, 1H), 4.42 (d of d, 1H), 5.51 (s, 2H), 5.55 (d, 1H), 5.62 (d, 1H), 7.34–7.48 (m, 2H) and 7.68–7.78 (m, 2H);

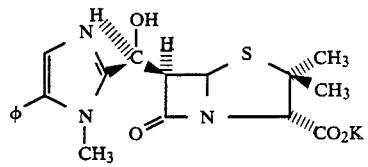

(D$_2$O) 1.41 (s, 3H), 1.61 (s, 3H), 3.66 (s, 3H), 4.23 (s, 1H), 4.32 (d of d, 1H), 5.27 (d, 1H), 5.38 (d, 1H), 7.0 (s, 1H), and 7.3–7.58 (m, 5H);

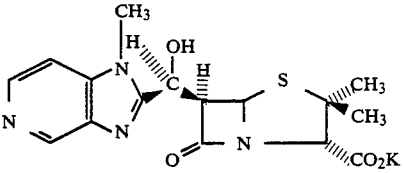

(D$_2$O) 1.40 (s, 3H), 1.61 (s, 3H), 3.93 (s, 3H), 4.28 (s, 1H), 4.44 (d of d, J=4 Hz, 11 Hz, 1H), 5.50 (d, J=4 Hz, 1H), 5.53 (d, J=11 Hz 1H), 7.61–7.63 (m, 1H), 8.34–8.36 (m, 1H) and 8.87 (s, 1H);

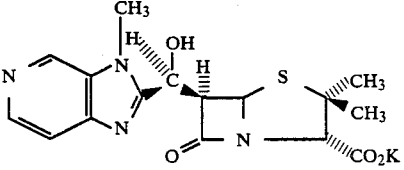

(D$_2$O) 1.40 (s, 3H), 1.63 (s, 3H), 4.03 (s, 3H), 4.29 (s, 1H), 4.46 (d of d, J=4 Hz, 10 Hz, 1H), 5.48 (d, J=4 Hz, 1H), 5.54 (d, J=10 Hz, 1H), 7.69 (d, 1H), 8.35 (d, 1H) and 8.91 (s, 1H).

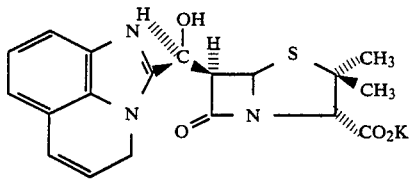

(D$_2$O) 1.41 (s, 3H), 1.62 (s, 3H), 4.28 (s, 1H), 4.41 (d of d, J=4 Hz, 11 Hz, 1H), 5.20 (s, 2H), 5.32 (d, J=11Hz, 1H), 5.46 (d, J=4Hz, 1H), 5.9–6.0 (m, 1H), 6.58–6.68 (m, 1H), 6.94 (d, 1H), 7.13 (t, 1H) and 7.4 (d, 1H).

EXAMPLE 16

6-beta-(2-Benzimidazolyl-(S)-hydroxy)methylpenicillanic Acid (R$^9$=H; R$^8$=H)

To 200 mg of the product of Example 1G in 20 ml of methanol and cooled to −78° C. was added a 20 ml portion of methylene chloride saturated with ozone and the reaction mixture stirred at −78° C. The solution was purged with nitrogen, 2 ml of dimethylsulfide was added and the reaction solution concentrated to dryness. The residue was dissolved in water, washed with ethyl acetate (2×75 ml) and freeze-dried, 185 mg. The solids were dissolved in methanol, 7 ml of the ozone/methylene chloride solution was added and the reaction worked up to give a yellow glass.

The reaction was repeated on 232 mg of starting reagent using 15 ml of methylene chloride saturated with ozone. On work-up there was obtained, when combined with the first run, 415 mg of crude product. Chromatographing on C-18 column with 10% acetonitrile in water there was obtained 135 mg of product as a white solid.

The NMR spectrum (300 MHz, D$_2$O) showed absorption at 1.42 (s, 3H), 1.63 (s, 3H), 4.26 (s, 1H), 4.3 (d of d, J=4 Hz, 10 Hz, 1H), 5.43 (d, J=4 Hz, 1H), 5.43 (d, J=10 Hz, 1H), 7.3–7.4 (m, 2H) and 7.6–7.7 (m, 2H) ppm.

EXAMPLE 17

6-beta-(2-[1-Methylbenzimidazolyl]-(S)-hydroxy)methylpenicillanic Acid (R$^9$=H, R$^8$=CH$_3$)

A. Allyl 6-beta-(2-[1-methylbenzimidazolyl]hydroxy)methyl-6-bromopenicillanate A solution of 18.88 g (0.0473 mole) allyl 6,6-dibromopenicillanate in 400 ml methylene chloride was cooled to −78° C. and 16.90 ml (0.0473 mole) 2.8M methylmagnesium bromide in ethyl ether was added. The mixture was stirred at −78° C. for 30 minutes, a solution of 7.58 g (0.0473 mole) 1-methylbenzimidazole-2-carboxaldehyde in 30 ml methylene chloride was added and stirring continued for an additional 30 minutes. Acetic acid (2.71 ml, 0.0473 mole) was added, the mixture poured into saturated ammonium chloride solution, the layers separated and the organic layer dried (MgSO$_4$). Evaporation of solvent afforded an orange oil in quantitative yield which was used without purification except that the last traces of chlorinated solvent were removed by evaporation of its solution in benzene.

B. Allyl 6-beta-(2-[1-methylbenzimidazolyl]-(S)-hydroxy)methylpenicillanate The product obtained in Example 17A was dissolved in 150 ml tetrahydrofuran, 25.45 ml (0.0946 mole) tri-n-butyltin hydride was added, the mixture refluxed for six hours and stirred overnight at room temperature. The solvent was evaporated in vacuo, the residue taken up in acetonitrile/hexanes and the acetonitrile washed with hexanes. The acetonitrile layer was evaporated to dryness in vacuo to afford 16.86 g brown oil which was purified by flash column chromatography on 600 g of silica gel, eluting with 30% ethyl acetate in chloroform (v/v) to obtain 2 fractions:

1. 3.64 g (20.8%) more polar isomer having 6 beta, 8S stereochemistry as determined by $^1$H-NMR at 300 MHz. $^1$H-NMR(CDCl$_3$)ppm(delta): 1.32 (s, 3H), 1.58 (s, 3H), 3.71 (s, 3H), 4.43 (s, 1H), 4.52 (dd, 1H), 4.58 (d, 2H), 5.16–5.42 (m, 3H), 5.49 (d, 1H), 5.76–5.94 (m, 1H), 7.06–7.26 (m, 3H), 7.52–7.60 (m, 1H). 2. 2.6 g (14.9%) less polar isomer.

C. 6-beta-(2-[1-methylbenzimidazolyl]-(S)-hydroxy)methylpenicillanic acid potassium salt To 3.64 g (0.0098 mole) of the above product from Example 17B in 20 ml ethyl acetate was added 360 mg tetrakis (triphenylphosphine)palladium (O), 360 mg triphenylphosphine and 19.6 ml potassium 2-ethylhexanoate solution and the mixture stirred at room temperature for one hour (nitrogen atmosphere). An excess of ethyl ether was added to precipitate the solid product which was collected by filtration and dried in vacuo to obtain 1.38 g of product. Addition of more ether to the mother liquors precipitated a second crop, 1.51 g. The two crops were combined and chromatographed, eluting with 15% acetonitrile in water (v/v) to obtain 1.37 g (35%) freeze-dried product as a pale yellow solid. 300 MHz $^1$H-NMR(D$_2$O)ppm(delta): 1.36 (s, 3H), 1.58 (s, H), 3.84 (s, 3H), 4.24 (s, 1H), 4.40 (dd, 1H), 5.38–5.48 (m, 2H), 7.22–7.38 (m, 2H), 7.44–7.54 (m, 1H), 7.6–8.7 (m, 1H). IR(KBr): 1610, 1750, 3440 cm$^{-1}$.

Analysis calculated for C$_{17}$H$_{18}$N$_3$O$_4$S.K.1.6 H$_2$O: C, 47.67; H, 4.99; N, 9.81%. Found: C, 47.74; H, 5.12; N, 9.73%.

EXAMPLE 18

5-Methyl-2-oxo-1,3-dioxolen-4-ylmethyl 6-beta-(2-[1-methylbenzimidazolyl]-(S)-hydroxy)methylpenicillanate

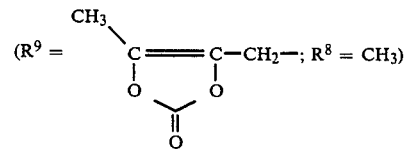

A mixture of 200 mg (0.5 mmole) of the product of Example 17C, 96 mg (0.5 mmole) 4-bromomethyl-5-methyl-2-oxo-1,3-dioxolene and 4 ml dimethylformamide was stirred at room temperature for 18 hours. The resulting mixture was poured into water, extracted three times with ethyl ether, the extracts dried (MgSO$_4$) and solvent evaporated to obtain a gold colored oil which gradually solidified in vacuo, 110 mg (46%).

300 MHz $^1$H-NMR(CDCl$_3$)ppm(delta): 1.34 (s, 3H), 1.62 (s, 3H), 2.16 (s, 3H), 3.82 (s, 3H), 4.46 (s, 1H), 4.52 (dd, 1H), 4.88 (AB quartet, 2H), 5.41 (d, 1H), 5.56 (d, H), 7.08–7.38 (m, 3H), 7.58–7.78 (m, 1H).

EXAMPLE 19

1-(Ethoxycarbonyloxy)ethyl 6-beta-(2-[1-methylbenzimidazolyl]-(S)-hydroxy)methylpenicillanate ($R^9$=C$_2$H$_5$OCO$_2$CH(CH$_3$)—; $R^8$=CH$_3$)

To a solution of 150 mg (0.374 mmole) of the product of Example 17C in 2 ml dimethylformamide was added 0.051 ml (0.374 mmole) 1-chloroethylethylcarbonate and 56 mg (0.374 mmole) sodium iodide. The mixture was stirred overnight, poured into water, extracted with ethyl ether, the extracts dried (MgSO$_4$) and solvent evaporated in vacuo to obtain 60 mg of product as a pale yellow oil, a mixture of two isomers.

300 MHz $^1$H-NMR(CDCl$_3$)ppm(delta): 1.04–1.34 (m, 3H), 1.41 (s, 1.5H), 1.42 (s, 1.5H), 1.52 (d, 1.5H), 1.54 (d, 1.5H), 1.61 (s, 1.5H), 1.63 (s, 1.5H), 3.82 (s, 3H), 4.08 (q, 1H), 4.18 (q, 1H), 4.41 (s, 0.5H), 4.46 (s, 0.5H), 4.52 (dd, 1H), 5.39 (d, 1H), 5.52 (d, 0.5H), 5.54 (d, 0.5H), 6.66–6.82 (m, 1H), 7.06–7.40 (m, 3H), 7.50–7.80 (m, 1H).

EXAMPLE 20

Starting with allyl 6,6-dibromopenicillanate and the appropriate aldehyde and employing the procedures of Examples 17A and 17B, the following (S) isomers were prepared:

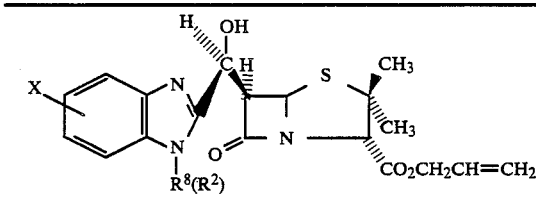

| X | $R^8$ ($R^2$) | NMR(300 MHz)CDCl$_3$,ppm |
|---|---|---|
| 5- and 6-CH$_3$ (mixture) | CH$_3$ | 1.42 (s, 3H), 1.68 (s, 3H), 2.46 (s, 1.5H), 2.5 (s, 1.5H), 3.82 (s, 3H), 4.52 (s, 3H), 4.6 (2dd, 1H), 4.7 (m, 2H), 5.2–5.7 (m, 4H), 5.8–6.05 (m, 1H), 7.0–7.3 (m, 2H), 7.4–7.7 (m, 1H). |
| 6-OCH$_3$ | CH$_3$ | 1.32 (s, 3H), 1.58 (s, 3H), 3.66 (s, 3H), 3.78 (s, 3H), 4.46 (s, 1H), 4.52 (dd, 1H), 4.6 (d, 1H), 5.2–5.4 (m, 3H), 5.5 (d, 1H), 5.8–6.0 (m, 1H), 6.48 (d, 1H), 6.86 (dd, 1H), 7.43 (d, 1H). |
| 5-F | CH$_3$ | 1.36 (s, 3H), 1.61 (s, 3H), 3.78 (s, 3H), 4.46 (s, 1H), 4.5 (d of d, 1H), 4.59 (d, 2H), 5.18–5.4 (m, 3H), 5.49 (d, 1H), 5.78–5.92 (m, 1H), 6.88–7.0 (m, 1H), 7.02–7.12 (m, 1H) and 7.2–7.3 (m, 1H). |
| 7-CH$_3$ | CH$_3$ | 1.37 (s, 3H), 1.62 (s, 3H), 2.53 (s, 3H), 3.90 (s, 3H), 4.28 (s, 1H), 4.57 (d of d, 1H), 4.63 (d, 2H), 5.22–5.4 (m, 3H), 5.53 (d, 1H), 5.8–5.98 (m, 1H), 6.88 (d, 1H), 7.05 (t, 1H) and 7.44 (d, 1H). |
| 5-OCH$_3$ | CH$_3$ | 1.28 (s, 3H), 1.54 (s, 3H), 3.68 (s, 3H), 3.72 (s, 3H), 4.4 (s, 1H), 4.52 (dd, 1H), 4.56 (m, 2H), 5.1–5.4 (m, 3H), 5.48 (d, 1H), 5.76–5.9 |

-continued

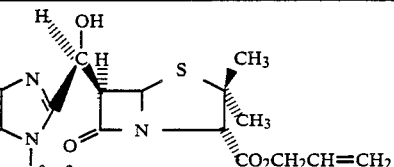

| X | $R^8$ ($R^2$) | NMR(300 MHz)CDCl$_3$,ppm |
|---|---|---|
| | | (m, 1H), 6.8 (dd, 1H), 6.96–7.1 (m, 1H), 7.28 (s, 1H). |
| 5-F | C$_2$H$_5$ | 1.38 (s, 3H), 1.44 (t, 3H), 1.62 (s, 3H), 4–4.52 (m, 2H), 4.46 (s, 1H), 4.54 (dd, 1H), 4.61 (d, 2H), 5.16–5.5 (m, 3H), 5.56 (d, 1H), 5.79–5.96 (m, 1H), 6.9–7.06 (m, 1H), 7.10–7.19 (m, 1H) and 7.24–7.34 (m, 1H). |
| 5- and 6-F (mixture) | FCH$_2$ | 1.42 (s, 3H), 1.63 (s, 3H), 4.41 (dd, 1H), 4.46 (s, 1H), 4.64 (d, 2H), 5.22–5.45 (m, 2H), 5.82–6.02 (m, 1H), 6.08–6.56 (m, 2H), 6.96–7.08 (m, 1H), 7.14 (dd, 1H) and 7.58 (dd, 1H). |
| 5- and 6-F (mixture) | CH$_2$C≡CH | 1.38 (s, 3H), 1.61 (s, 3H), 2.40 (m, 1H), 4.43 (dd, J=4 Hz, 10 Hz, 1H), 4.46 (s, 1H), 5.0–5.46 (m, 4H), 5.52 (d, J=10 Hz, 1H), 5.59 (d, J=4 Hz, .6×1H), 5.59 (d, J=4 Hz, .4×1H), 5.84–6.02 (m, 1H), 6.98–7.2 (m, 2H) and 7.36–7.66 (m, 1H). |
| 5,6-F$_2$ | CH$_3$ | 1.38 (s, 3H), 1.62 (s, 3H), 3.81 (s, 3H), 4.44–4.46 (m, 1H), 4.45 (s, 1H), 4.6–4.63 (m, 2H), 5.26–5.4 (m, 3H), 5.55 (d, J=4.5 Hz, 1H), 5.9–6.0 (m, 1H), 7.04–7.14 (m, 1H) and 7.4–7.54 (m, 1H). |
| 7-F | CH$_3$ | 1.42 (s, 3H), 1.66 (s, 3H), 4.14 (s, 3H), 4.48 (s, 1H), 4.58 (dd, J=4 Hz, 10 Hz, 1H), 4.64 (d, 2H), 5.26–5.31 (m, 1H), 5.51 (d, J=10 Hz, 1H), 5.63 (d, J=4 Hz, 1H), 5.84–6.0 (m, 1H), 6.09–7.07 (m, 1H), 7.16–7.26 (m, 1H) and 7.52 (d, 1H). |

EXAMPLE 21

Starting with the appropriate allyl ester and employing the procedure of Example IG, the following final products were prepared:

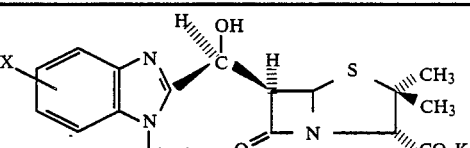

| X | $R^8$ ($R^2$) | NMR(300 MHz)D$_2$O, ppm |
|---|---|---|
| H | CH$_3$ | 1.26 (s, 3H), 1.48 (s, 3H), 3.76 (s, 3H), 4.16 (s, 1H), 4.36 (dd, 1H), 5.3–5.45 (m, 2H), 7.2–7.3 (m, 2H), 7.3–7.6 (m, 2H). |
| 5-F | C$_2$H$_5$ | 1.41 (s, 3H), 1.46 (t, 3H), 1.62 (s, 3H), 1.28 (s, 1H), 4.32–4.48 (m, 2H), 4.42 (dd, 1H), 5.46 (d, 1H), 5.49 (d, 1H), 7.12–7.24 (m, 1H), 7.34– |

-continued

| X | $R^8$ ($R^2$) | NMR(300 MHz)$D_2O$, ppm |
|---|---|---|
|  |  | 7.44 (m, 1H) and 7.52–7.64 (m, 1H). |
| 5- and 6-F (mixture) | $FCH_2$ | 1.44 (s, 3H), 1.64 (s, 3H), 4.11 (s, 1H), 4.44 (dd, 1H), 5.54 (d, 1H), 5.57 (d, 1H), 6.43 (ab q, 2H), 7.14–7.28 (m, 1H), 7.57 (dd, 1H) and 7.72 (dd, 1H). |
| 5- and 6-F mixture | $CH_2C\equiv CH$ | 1.38 (s, 3H), 1.58 (s, 3H), 2.81 (m, 1H), 4.27 (s, 1H), 4.37–4.42 (m, 1H), 5.10 (d, 2H), 5.49–5.54 (m, 2H), 7.05–7.13 (m, 1H), 7.31–7.37 (m, 1H), 7.5–7.55 (m, .4×1H) and 7.57–7.61 (m, .6×1H). |
| $5,6-F_2$ | $CH_3$ | 1.41 (s, 3H), 1.62 (s, 3H), 3.88 (s, 3H), 4.28 (s, 1H), 4.39–4.44 (m, 1H), 5.45–5.47 (m, 2H), 7.47–7.57 (m, 1H) and 7.67–7.71 (m, 1H). |
| 7-F | $CH_3$ | 1.41 (s, 3H), 1.62 (s, 3H), 4.08 (s, 3H), 4.28 (s, 1H), 4.42 (dd, J=4 Hz, 10 Hz, 1H), 5.47 (d, J=10 Hz, 1H), 5.47 (d, J=4 Hz, 1H), 7.07–7.13 (m, 1H), 7.24–7.27 (m, 1H) and 7.46–7.50 (m, 1H). |
| H | $C_2H_5$ | 1.4–1.45 (m, 6H), 1.6 (s, 3H), 4.3 (s, 1H), 4.3–4.75 (m, 3H), 5.4–5.6 (m, 2H), 7.3–7.5 (m, 2H), 7.6 (d, 1H), 7.7 (d, 1H). |
| 5- and 6-$CH_3$ (mixture) | $CH_3$ | 1.32 (s, 3H), 1.54 (s, 3H), 2.36 (s, 1.5H), 2.38 (s, 1.5H), 3.76 (s, 3H), 4.2 (s, 1H), 4.36 (dd, 1H), 5.4 (d, 1H), 5.42 (d, 1H), 7.06–7.6 (m, 3H). |
| 6-$OCH_3$ | $CH_3$ | 1.35 (s, 3H), 1.57 (s, 3H), 3.84 (s, 3H), 3.88 (s, 3H), 4.23 (s, 1H), 4.37 (dd, 1H), 5.4 (d, 1H), 5.44 (d, 1H), 6.48 (dd, 1H), 7.12 (d, 1H), 7.57 (d, 1H). |
| 5-$OCH_3$ | $CH_3$ | 1.35 (s, 3H), 1.56 (s, 3H), 4.24 (s, 1H), 4.38 (dd, 1H), 5.20 (d, 1H), 5.22 (d, 1H), 7.04 (m, 1H), 7.22 (m, 1H), 7.48 (d, 1H). |
| 5-F | $CH_3$ | ($CDCl_3$) 1.38 (s, 3H), 1.69 (s, 3H), 3.89 (s, 3H), 4.24 (s, 1H), 4.39 (d of d, 1H), 5.4–5.47 (m, 2H), 7.1–7.22 (m, 1H), 7.32–7.4 (m, 1H) and 7.48–7.58 (m, 1H). |
| 7-$CH_3$ | $CH_3$ | 1.39 (s, 3H), 1.61 (s, 3H), 2.74 (s, 3H), 4.10 (s, 3H), 4.26 (s, 1H), 4.41 (d of d, 1H), 5.4–5.5 (m, 2H), 7.08 (d, 1H), 7.1–7.22 (m, 1H) and 7.5 (d, 1H). |

EXAMPLE 22

1-(Ethoxycarbonyloxy)-(S)-ethyl 6-beta-(2-[1-vinylbenzimidazolyl]-(S)-hydroxy)methylpenicillanate (R=(S) $C_2H_5O_2COCh(CH_3)$—; $R^2=CH_2=CH$—)

A. tetra-n-butylammonium 6,6-dibromopenicillanate

To a solution of 250 ml of methylene chloride and 180 ml of water containing 36 g of 6,6-dibromopenicillanic acid was added 8.4 g of sodium bicarbonate followed by tetra-n-butylammonium sulfate in portions. The pH was maintained at 7–7.5 by the addition of a 2N sodium hydroxide solution. After the addition was complete, the mixture was stirred for 20 minutes. The separated organic phase was washed with water, dried over magnesium sulfate and concentrated to an orange oil.

B. 1-(ethoxycarbonyloxy)-(S) and (R)-ethyl 6,6-dibromopenicillanate

To 250 ml of acetone was added 59.2 g of tetra-nbutylammonium 6,6-dibromopenicillanate, 15.2 g of alphachlorodiethyl carbonate and 15 g of sodium iodide and the reaction mixture allowed to stir at room temperature overnight. The acetone was removed in vacuo and the residue taken up in ethyl acetate. The organic solution was washed with water (3×), dried over magnesium sulfate and concentrated to a dark oil. The residue was extracted with ether, which on concentration gave a yellow oil. Treatment of a ether solution (200 ml) of the oil with hexane gave 2.2 g of the (S) isomer. Concentration of the filtrate and reconstitution in 25 ml of ether followed by the addition of 25 ml of hexane gave an additional 2.5 g of (S) isomer. The filtrate was stripped to dryness and allowed to stand for two weeks. The crystallized material was recrystallized from etherhexane to give 4.42 g of the (R) isomer.

$^1$H-NMR(300 MHz, $CDCl_3$) (S) isomer: 1.29 (t, 3H), 1.47 (s, 3H), 1.55 (d, 3H), 1.58 (s, 3H), 4.2 (q, 2H), 4.48 (s, 1H), 5.76 (s, 1H) and 6.77 (q, 1H) ppm.

$^1$H-NMR(300 MHz, $CDCl_3$) (R) isomer: 1.32 (t, 3H), 1.5 (s, 3H), 1.56 (d, 3H), 1.61 (s, 3H), 4.25 (q, 2H), 4.5 (s, 1H), 5.77 (s, 1H) and 6.8 (q, 1H) ppm.

C. 1-(ethoxycarbonyloxy)-(S)-ethyl 6-(2-[1-vinylbenzimidazolyl]hydroxy)methyl-6-bromopenicillanate Starting with 4.75 g of 1-(ethoxycarbonyloxy)-(S)-ethyl 6,6-dibromopenicillanate, 3.75 ml of methyl magnesium bromide (2.8M in ether), 1.72 g of 1-vinylbenzimidazole-2-carboxyaldehyde and following the procedure of Example 1E, the product was obtained as an orange glass.

D. 1-(ethoxycarbonyloxy)-(S)-ethyl 6-beta-(2-[1-vinylbenzimidazolyl]-(S)-hydroxy)methylpenicillanate To the product from Example 22C in 50 ml of benzene was added 26.9 ml of tri-n-butyltin hydride and the reaction refluxed for 6 hours. After standing at room temperature overnight, the benzene was removed and the residue dissolved in acetonitrile. The acetonitrile solution was washed with hexane and concentrated to give an orange oil, which was chromatographed on 150 g of silica gel using 10% ethyl acetate in chloroform as the eluent to give 750 mg of the (6-beta, 8-(S), (S)-Bac) isomer, 458 mg of the (6-beta, 8-(R), (S)-Bac) isomer and 819 mg of a crude 1:1 mixture of isomers.

The NMR spectrum (300 MHz, CDCl₃) of the desired (6-beta, 8-(S), (S)-Bac) isomer showed absorption at 1.28 (t, 3H), 1.44 (s, 3H), 1.55 (d, 3H), 1.6 (s, 3H), 4.19 (q, 2H), 4.41 (s, 1H), 4.54 (dd, 1H), 5.3–5.7 (m, H), 5.32 (d, 1H), 5.73 (d, 1H), 6.76 (q, 1H), 7.2–7.4 (m, 3H), 7.5–7.6 (m, 1H) and 7.7–7.8 (m, 1H) ppm.

EXAMPLE 23

1-(Ethoxycarbonyloxy)-(S)-ethyl 6-beta-(2-[1-vinyl-benzimidazolyl]-(S)-hydroxy)methylpenicillanate tosylate salt To 50 mg of the product of Example 22D in 25 ml of ether was added 17.6 mg of dry p-toluenesulfonic acid in 3 ml of ether and the mixture allowed to stir for 10 minutes. The solids were filtered under nitrogen and dried, 42 mg.

The NMR spectrum (300 MHz, CDCl₃) showed absorption at 1.26 (t, 3H), 1.4 (s, 3H), 1.52 (d, 3H), 1.58 (s, 3H), 2.32 (s, 3H), 3.72 (d, 1H), 4.17 (q, 2H), 4.41 (s, 1H), 4.89 (d of d, J=4 Hz, 10 Hz, 1H), 5.38 (d, J=4 Hz, 1H), 5.59 (d, J=10 Hz, 1H), 5.9–6.0 (m, 2H), 6.71 (q, 1H), 7.12 (d, 2H), 7.18–7.3 (m, 1H), 7.5–7.7 (m, 3H), 7.74 (d, 2H), 7.7–7.8 (m, 1H) and 7.8–7.9 (m, 1H) ppm.

EXAMPLE 24

1-(Ethoxycarbonyloxy)-(S)-ethyl 6-beta-(2-[1-vinylbenzimidazolyl]-(S)-hydroxy)methylpenicillanate mesylate salt To 100 mg of the product of Example 22D in 25 ml of ether was added 19.2 mg of methanesulfonic acid in 1 ml of ether. After stirring for 30 minutes the solids were filtered under nitrogen and dried, 93 mg.

The NMR spectrum (300 MHz, CDCl₃) showed absorption at 1.27 (t, 3H), 1.41 (s, 3H), 1.53 (d, 3H), 1.6 (s, 3H), 2.83 (s, 3H), 3.72 (d, 1H), 4.18 (q, 2H), 4.42 (s, 1H), 4.86 (d of d, J=6 Hz, 10 Hz, 1H), 5.44 (d, J=6 Hz, 1H), 5.56 (d, J=10 Hz, 1H), 5.9–6.1 (m, 2H), 6.7–6.8 (m, 1H), 7.2–7.3 (m, 1H), 7.5–7.7 (m, 1H) and 7.9–8.0 (m, 1H) ppm.

EXAMPLE 25

Employing the procedure of Example 19 and starting with the appropriate potassium and halide, the following esters were prepared:

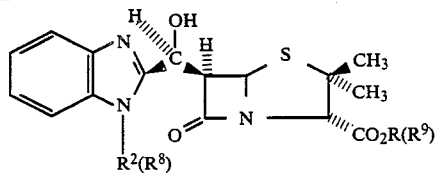

| $R^2(R^8)$ | $R(R^9)$ | NMR(300 MHz), ppm |
|---|---|---|
| CH₃SCH₂ | CH₂O₂CC₂H₅ | (CDCl₃) 1.14 (t, 3H), 1.42 (s, 3H), 1.64 (s, 3H), 2.06 (s, 3H), 2.36 (q, 2H), 4.49 (s, 1H), 4.5 (dd, 1H), 5.36 (ab q, 2H), 5.58 (d, 1H), 5.66 (d, 1H), 5.78 (ab q, 2H), 7.18–7.36 (m, 2H), 7.36–7.56 (m, 1H) and 7.56–7.78 (m, 1H); |
| C₂H₅ | CH(CH₃)O₂CCH₃ | (CDCl₃) 1.47 (t, 3H), 1.47 (s, .5×3H), 1.49 (s, .5×3H), 1.53 (d, .5×3H), 1.55 (d, .5×3H), 1.66 (s, .5×3H), 1.68 (s, .5×3H), 4.16–4.5 (m, 2H), 4.44 (s, .5×1H), 4.48 (s, .5×1H), 4.58 (dd, 1H), 5.44 (d, 1H), 5.6 (d, .5×1H), 5.62 (d, .5×1H), 6.8–6.94 (m, 1H), 7.16–7.38 (m, 2H), 7.38–7.58 (m, 1H) and 7.58–7.76 (m, 1H); |
| CH₃SCH₂ | CH₂O₂CC(CH₃)₃ | (CDCl₃) 1.2 (s, 9H), 1.42 (s, 3H), 1.62 (s, 3H), 2.08 (s, 3H), 4.45 (s, 1H), 4.49(dd, 1H), 5.37 (ab q, 2H), 5.51 (d, 1H), 5.62 (d, 1H), 5.8 (ab q, 2H), 7.12–7.36 (m, 2H), 7.36–7.55 (m, 1H) and 7.55–7.75 (m, 1H); |
| CH₃SCH₂ | CH(CH₃)O₂CCH₃ | (CDCl₃) 1.43 (s, .5×3H), 1.44 (s, .5×3H), 1.49 (d, .5×3H), 1.52 (d, .5×3H), 1.62 (s, .5×3H), 1.64 (s, .5×3H), 2.06 (s, 3H), 4.42 (s, .5×1H), 4.46 (s, .5×1H), 4.5 (dd, 1H), 5.34 (ab q, 2H), 5.56 (d, 1H), 5.62 (d, .5×1H), 5.64 (d, .5×1H), 6.76–6.93 (m, 1H), 7.14–7.34 (m, 2H), 7.34–7.54 (m, 1H) and 7.54–7.78 (m, 1H); |
| C₂H₅ | CH₂O₂C(CH₂)₄CO₂<br>\|<br>C₆H₅CH₂ | (CDCl₃) 1.33 (s, 3H), 1.4 (t, 3H), 1.57 (s, 3H), 1.54–1.72 (m, 4H), 2.22–2.4 (m, 4H), 4.0–4.4 (m, 2H), 4.44 (s, 1H), 4.56 (dd, 1H), 5.04 (s, 2H), 5.34 (d, 1H), 5.5 (d, 1H), 5.72 (ab q, 2H), 7.06–7.5 (m, 8H) and 7.5–7.64 (m, 1H); |
| FCH₂ | CH₂O₂C(CH₂)₄CO₂<br>\|<br>C₆H₅CH₂ | (CDCl₃) 1.4 (s, 3H), 1.62 (s, 3H), 1.54–1.74 (m, 4H), 2.26–2.44 (m, 4H), 4.44 (dd, 1H), 4.46 (s, 1H), 5.08 (s, 2H), 5.56 (d, 1H), 5.6 (d, 1H), 6.1–6.56 (m, 2H), 7.2–7.66 (m, 8H), 7.66–7.74 (m, 1H) and 7.76 (ab q, 2H) |

-continued

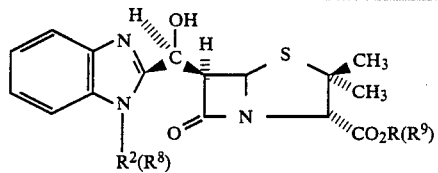

| R²(R⁸) | R(R⁹) | NMR(300 MHz), ppm |
|---|---|---|
| $C_2H_5$ | CH(CH₃)OC(O)—OCH(CH₃)₂ | (CDCl₃) 1.21–1.37 (m, 6H), 1.37–1.8 (m, 12H), 4.18–4.5 (m, 2H), 4.42 (s, .5×1H), 4.48 (s, .5×1H), 4.54 (dd, 1H), 4.8–4.96 (m, 1H), 5.35–5.51 (m, 1H), 5.61 (d, .5×1H), 5.64 (d, .5×1H), 6.7–6.84 (m, 1H), 7.12–7.38 (m, 3H) and 7.6–7.78 (m, 1H); |
| $C_2H_5$ | CH(CH₃)OC(O)—OC₂H₅ | (CDCl₃) 1.32 (t, 3H), 1.38–1.76 (m, 12H), 4.1–4.34 (m, 3H), 4.34–4.52 (m, 1H), 4.44 (s, .5×1H), 4.5 (s, .5×1H), 4.58 (dd, 1H), 5.4 (d, 1H), 5.61 (d, .5×1H), 5.63 (d, .5×1H), 6.72–6.86 (m, 1H), 7.16–7.4 (m, 2H), 7.4–7.58 (m, 1H) and 7.58–7.8 (m, 1H); |
| $CH_2C\equiv CH$ | CH₂C(O)N(CH₃)₂ | (CDCl₃) 1.6 (s, 3H), 1.73 (s, 3H), 2.34–2.42 (m, 1H), 2.96 (s, 3H), 2.98 (s, 3H), 4.47 (dd, 1H), 4.54 (s, 1H), 4.79 (ab q, 2H), 5.13 (2×ab q, J=4 Hz, 2H), 5.62 (d, 1H), 5.64 (d, 1H), 7.18–7.38 (m, 2H), 7.38–7.52 (m, 1H) and 7.64–7.88 (m, 1H); |
| $CH_2C\equiv CH$ | CH₂O₂CC₂H₅ | (CDCl₃) 1.43 (s, 3H), 1.66 (s, 3H), 2.12–2.45 (m, 3H), 4.48 (s, 1H), 4.49 (dd, 1H), 5.14 (2×ab q, J=4 Hz, 2H), 5.61 (d, 1H), 5.64 (d, 1H), 5.8 (ab q, 2H), 7.2–7.36 (m, 2H), 7.41–7.5 (m, 1H), and 7.67–7.74 (m, 1H); |
| $CH_2C\equiv CH$ | (phthalidyl) | (CDCl₃) 1.49 (s, .5×3H), 1.52 (s, .5×3H), 1.62 (s, .5×3H), 1.64 (s, .5×3H), 2.37 (m, 1H), 4.42–4.72 (m, 2H), 4.54 (s, .5×1H), 4.57 (s, .5×1H), 4.92–5.3 (m, 2H), 5.54 (d, .5×1H), 5.56 (d, .5×1H), 5.58 (d, .5×1H), 5.62 (d, .5×1H), 7.18–7.37 (m, 2H), 7.37–7.53 (m, 2H), 7.53–7.9 (m, 4H) and 7.9–8.04 (m, 1H); |
| $CH_2C\equiv CH$ | (5-methyl-2-oxo-1,3-dioxolen-4-yl)methyl | (CDCl₃) 1.38 (s, 3H), 1.66 (s, 3H), 2.2 (s, 3H), 2.32–2.42 (m, 1H), 4.44–4.56 (m, 2H), 4.92 (ab q, 2H), 5.12 (2×ab q, J=4 Hz, 2H), 5.58 (d, 1H), 5.64 (d, 1H), 8.2–8.38 (m, 2H), 8.38–8.5 (m, 1H) and 8.6–8.76 (m, 1H); |
| $CH_2F$ | (5-methyl-2-oxo-1,3-dioxolen-4-yl)methyl | (CDCl₃) 1.4 (s, 3H), 1.66 (s, 3H), 2.2 (s, 3H), 4.44 (dd, 1H), 4.49 (s, 1H), 4.91 (ab q, 2H), 5.61 (d, 1H), 5.65 (d, 1H), 6.1–6.54 (m, 2H), 7.26–7.5 (m, 3H) and 7.66–7.79 (m, 1H); |
| $C_2H_5$ | CH₂O₂CC₂H₅ | (CDCl₃) 1.14 (t, 3H), 1.4 (s, 3H), 1.46 (t, 3H), 1.64 (s, 3H), 2.38 (q, 2H), 4.14–4.44 (m, 2H), 4.45 (s, 1H), 4.56 (dd, 1H), 5.4 (d, 1H), 5.58 (d, 1H), 5.77 (ab q, 2H), 7.14–7.56 (m, 3H) and 7.56–7.8 (m, 1H); |
| $FCH_2$ | CH(CH₃)O₂CCH₃ | (CDCl₃) 1.48 (s, .5×3H), 1.49 (s, .5×3H), 1.54 (d, .5×3H), 1.56 (d, .5×3H), 1.66 (s, .5×3H), 1.68 (s, .5×3H), 2.08 (s, .5×3H), 2.09 (s, .5×3H), 4.46 (s, .5×1H), 4.48 (dd, 1H), 4.51 (s, .5×1H), 4.62 (d, 1H), 4.66 (d, 1H), 6.12–6.6 (m, 2H), 6.84–6.98 (m, 1H) and 7.26–7.8 (m, 4H); |
| $FCH_2$ | CH₂O₂CC₂H₅ | (CDCl₃) 1.18 (t, 3H), 1.46 (s, 3H), 1.68 (s, 3H), 2.4 (q, 2H), 4.45 (dd, 1H), 4.51 (s, 1H), 5.61 (d, 1H), 5.64 (d, 1H), 5.8 (ab q, 2H), 6.12–6.6 (m, 2H), 7.2–7.58 (m, 3H) and 7.58–7.8 (m, 1H); |

-continued

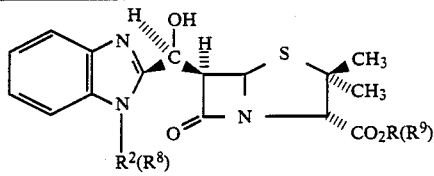

| $R^2(R^8)$ | $R(R^9)$ | NMR(300 MHz), ppm |
|---|---|---|
| FCH$_2$ | ![phthalide] | (CDCl$_3$) 1.5 (s, .5×3H), 1.54 (s, .5×3H), 1.62 (s, .5×3H), 1.65 (s, .5×3H), 4.41 (dd, .5×1H), 4.44 (dd, .5×1H), 4.52 (s, .5×1H), 4.55 (s, .5×1H), 5.52–5.68 (m, 2H), 6.1–6.56 (m, 2H) and 7.16–8.0 (m, 8H); |
| FCH$_2$ | CH$_2$O$_2$CC(CH$_3$)$_3$ | (CDCl$_3$) 1.2 (s, 9H), 1.44 (s, 3H), 1.64 (s, 3H), 4.44 (dd, 4H), 4.48 (s, 1H), 5.6 (d, 1H), 5.64 (d, 1H), 5.8 (ab q, 2H), 6.1–6.6 (m, 2H) and 7.24–7.8 (m, 4H); |
| FCH$_2$ | CH(CH$_3$)OCOC$_2$H$_5$ | (CDCl$_3$) 1.22–1.36 (m, 3H), 1.36–1.74 (m, 9H), 3.4–3.78 (m, 2H), 4.4–4.52 (m, 2H), 5.46–5.66 (m, 2H), 6.1–6.58 (m, 2H), 6.7–6.82 (m, 1H), 7.2–7.56 (m, 3H) and 7.56–8.01 (m, 1H); |
| C$_2$H$_5$ | CH$_2$—C(CH$_3$)=... (cyclic carbonate) | (CDCl$_3$) 1.37 (s, 3H), 1.48 (t, 3H), 1.65 (s, 3H), 2.19 (s, 3H), 2.9 (d, 1H), 4.18–4.46 (m, 2H), 4.49 (s, 1H), 4.58 (dd, 1H), 4.91 (ab q, 2H), 5.44 (d, 1H), 5.62 (d, 1H), 7.2–7.4 (m, 3H) and 7.66–7.76 (m, 1H); |
| CH$_3$SCH$_2$ | ![phthalide] | (CDCl$_3$) 1.48 (s, .5×3H), 1.52 (s, .5×3H), 1.6 (s, .5×3H), 1.64 (s, .5×3H), 2.07 (s, 3H), 2.89 (d, 1H), 4.47–4.68 (m, 2H), 5.4 (ab q, 2H), 5.54–5.76 (m, 2H), 7.2–7.84 (m, 8H) and 7.94 (d, 1H); |
| C$_2$H$_5$ | ![phthalide] | (CDCl$_3$) 1.5 (t, 3H), 1.51 (s, .5×3H), 1.54 (s, .5×3H), 1.63 (s, .5×3H), 1.66 (s, .5×3H), 4.24–4.51 (m, 2H), 4.54 (s, .5×1H), 4.58 (s, .5×1H), 5.48 (d, 1H), 5.52 (d, 1H), 5.68 (d, .5×1H), 7.2–7.8 (m, 8H) and 7.94 (d, 1H); |
| CH$_3$SCH$_2$ | CH(CH$_3$)OCOC$_2$H$_5$ | (CDCl$_3$) 1.31 (t, .5×3H), 1.32 (t, .5×3H), 1.47 (s, .5×3H), 1.48 (s, .5×3H), 1.56 (d, .5×3H), 1.58 (d, .5×3H), 1.64 (s, .5×3H), 1.66 (s, .5×3H), 2.09 (s, 3H), 4.14–4.29 (m, 2H), 4.45 (s, .5×1H), 4.5 (s, .5×1H), 4.53 (dd, 1H), 5.3 (d, 1H), 5.44–5.76 (m, 3H), 6.79 (t, 1H), 7.3 (t, 1H), 7.4 (d, 1H) and 7.74 (d, 1H); |
| CH$_2$C≡CH | CH$_2$O$_2$C(CH$_2$)$_4$CO$_2$K | (D$_2$O) 1.4 (s, 3H), 1.45–1.62 (m, 4H), 1.66 (s, 3H), 2.07 (m, 1H), 2.08–2.2 (m, 2H), 2.4–2.5 (m, 2H), 4.51 (dd, J=4 Hz, 10 Hz, 1H), 4.76 (s, 1H), 5.25 (s, 2H), 5.6 (d, J=10 Hz, 1H), 5.62 (d, J=4 Hz, 1H), 5.87 (ab q, J$_{AB}$=6 Hz, 2H), 7.36–7.53 (m, 2H) and 7.7–7.8 (m, 2H); |
| CH$_2$C≡CH | CH$_2$O$_2$CC(CH$_3$)$_3$ | (CDCl$_3$) 1.187 (s, 9H), 1.43 (s, 3H), 1.66 (s, 3H), 2.33 (m, 1H), 4.5 (s, 1H), 4.5 (dd, J=4 Hz, 8 Hz, 1H), 5.2 (ab q, J=10 Hz, 2H), 5.7 (d, J=4 Hz, 1H), 5.68 (d, J=8 Hz, 1H), 5.8 (ab q, J=5.5 Hz, 2H), 7.3–7.37 (m, 2H), 7.5–7.53 (m, 1H) and 775–7.77 (m, 1H); |
| CH$_2$C≡CH | CH(CH$_3$)O$_2$CCH$_3$ | (CDCl$_3$) 1.42 (s, .5×3H), 1.43 (s, .5×3H), 1.49 (d, .5×3H), 1.51 (d, .5×3H), 1.62 (s, .5×3H), 1.64 (s, .5×3H), 2.05 (s, .5×3H), 2.06 (s, .5×3H), 2.34 (m, 1H), 4.4 (s, .5×1H), 4.45 (s, .5×1H), 4.46 (dd, 1H), 4.84–5.24 (m, 2H), 5.48–5.66 (m, 2H), 6.78– |

-continued

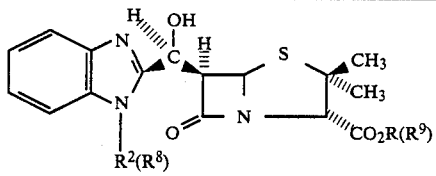

| $R^2(R^8)$ | $R(R^9)$ | NMR(300 MHz), ppm |
|---|---|---|
| | | 6.9 (m, 1H), 7.2–7.3 (m, 2H), 7.4 (d, 1H) and 7.66 (d, 1H); |
| $CH_2C\equiv CH$ | $CH(CH_3)OCOC_2H_5$ (C=O) | (CDCl$_3$) 1.44 (s, .5×3H), 1.46 (s, .5×3H), 1.56 (d, .5×3H), 1.58 (d, .5×3H), 1.64 (s, .5×3H), 1.66 (s, .5×3H), 2.38 (m, 1H), 4.21 (q, .5×2H), 4.22 (q, .5×2H), 4.44 (s, .5×1H), 4.49 (s, .5×1H), 4.5 (dd, J=4 Hz, 8 Hz, 1H), 4.9–5.26 (m, 2H), 5.48–5.66 (m, 2H), 6.7–6.82 (m, 1H), 7.1–7.34 (m, 2H), 7.4 (d, 1H) and 7.64 (d, 1H); |
| $CH_2C\equiv CH$ | $CH(CH_3)OCOCH(CH_3)_2$ (C=O) | (CDCl$_3$) 1.26 (d, .5×6H), 1.28 (d, .5×6H), 1.42 (s, .5×3H), 1.43 (s, .5×3H), 1.53 (d, .5×3H), 1.55 (d, .5×3H), 1.6 (s, .5×3H), 1.62 (s, .5×3H), 2.35 (m, 1H), 4.4 (s, .5×1H), 4.45 (s, .5×1H), 4.46 (dd, J=4 Hz, 10 Hz, 1H), 4.76–4.92 (m, 1H), 4.92–5.24 (m, 2H), 5.46–5.64 (m, 2H), 6.66–6.8 (m, 1H), 7.1–7.3 (m, 2H), 7.37 (d, 1H) and 7.62 (d, 1H); |
| $CH=CH_2$ | $CH_2CN(CH_3)_2$ (C=O) | (CDCl$_3$) 1.58 (s, 3H), 1.69 (s, 3H), 2.94 (s, 3H), 2.96 (s, 3H), 3.14 (d, 1H), 4.51 (s, 1H), 5.43 (dd, J=4.5 Hz, 10 Hz, 1H), 4.79 (ab q, J=14.5 Hz, 2H), 5.32 (d, 1H), 5.47 (dd, J=4 Hz, 10 Hz, 1H), 5.59 (d, J=4.5 Hz, 1H), 5.68 (d, 1H), 7.2–7.4 (m, 3H), 7.56–7.58 (m, 1H) and 7.71–7.74 (m, 1H); |
| $CH=CH_2$ | (phthalide group) | (CDCl$_3$) 1.45 (s, .5×3H), 1.49 (s, .5×3H), 1.58 (s, .5×3H), 1.61 (s, .5×3H), 4.51 (s, .5×1H), 4.54 (s, .5×1H), 4.48–4.64 (m, 1H), 5.28–5.7 (m, 4H) and 7.2–8.0 (m, 10H); |
| $CH=CH_2$ | $CH(CH_3)OCOC_2H_5$ (C=O) | (CDCl$_3$) 1.09 (t, 3H), 1.38 (s, .5×3H), 1.40 (s, .5×3H), 1.47–1.50 (m, 3H), 1.57 (s, .5×3H), 1.59 (s, .5×3H), 2.3 (q, 2H), 4.39 (s, .5×1H), 4.44 (s, .5×1H), 4.57 (dd, 1H), 5.26–5.44 (m, 2H), 5.52 (d, J=4.5 Hz, .5×1H), 5.53 (d, J=4.5 Hz, .5×1H), 5.67 (d, 1H), 6.78–6.9 (m, 1H), 7.16–7.22 (m, 3H), 7.4–7.5 (m, 1H) and 7.6–7.7 (m, 1H); |
| $CH=CH_2$ | $CH(CH_3)O_2CCH_3$ | (CDCl$_3$) 1.39 (s, .5×3H), 1.4 (s, .5×3H), 1.48 (d, .5×3H), 1.49 (d, .5×3H), 1.58 (s, .5×3H), 1.6 (s, .5×3H), 2.04 (s, 3H), 4.39 (s, .5×1H), 4.44 (s, .5×1H), 4.57 (dd, J=16 Hz, 1H), 5.32–5.43 (m, 2H), 5.52–5.54 (m, 1H), 5.67 (d, 1H), 6.84–6.87 (m, 1H), 7.23–7.31 (m, 3H), 7.48–7.50 (m, 1H) and 7.66–7.69 (m, 1H); |
| $CH=CH_2$ | $CH_2O_2CC_2H_5$ | (CDCl$_3$) 1.12 (t, 3H), 1.37 (s, 3H), 1.59 (s, 3H), 2.36 (q, 2H), 4.45 (s, 1H), 4.58 (dd, J=6 Hz, 10 Hz, 1H), 4.77 (s, 1H), 5.3–5.46 (m, 2H), 5.52 (d, J=6 Hz, 1H), 5.6–5.9 (m, 3H), 7.1–7.3 (m, 2H), 7.4–7.5 (m, 1H) and 7.6–7.7 (m, 1H); |
| $CH=CH_2$ | $CH_2O_2C(CH_2)_4CO_2K$ | (D$_2$O) 1.35 (s, 3H), 1.52–1.56 (m, 4H), 1.61 (s, 3H), 2.1–2.15 (m, 2H), 2.42–2.46 (m, 2H), 4.53–4.57 (m, 1H), 4.72 (s, 1H), 5.45–5.61 (m, 3H), 5.76–5.89 (m, 3H), 7.2–7.3 (m, 1H), 7.36–7.47 (m, 2H) and 7.74–7.77 (m, 2H); |
| $CH_3$ | $CH_2O_2CC(CH_3)_3$ | (CDCl$_3$) 1.22 (s, 9H), 1.44 (s, 3H), 1.66 (s, 3H), 2.92 (d, 1H), 3.86 (s, 3H), 4.52 (s, 1H), 4.59 (dd, 1H), 5.46 (d, 1H), 5.61 (d, 1H), 5.82 (ab q, 2H), 7.12–7.38 (m, 3H) and 7.6–7.76 (m, 1H); |

-continued

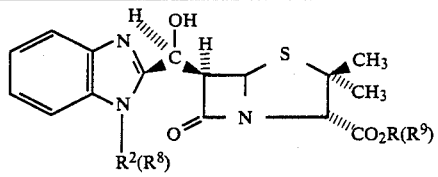

| $R^2(R^8)$ | $R(R^9)$ | NMR(300 MHz), ppm |
|---|---|---|
| $CH_3$ | (methyl dioxolenone CH₂ group) | (CDCl₃) 1.34 (s, 3H), 1.62 (s, 3H), 2.16 (s, 3H), 3.82 (s, 3H), 4.46 (s, 1H), 4.52 (dd, 1H), 4.88 (ab q, 2H), 5.41 (d, 1H), 5.56 (d, 1H), 7.08–7.38 (m, 3H) and 7.58–7.78 (m, 1H); |
| $CH_3$ | $CH(CH_3)OCOC_2H_5$ | (CDCl₃) 1.04–1.34 (m, 3H), 1.41 (s, .5×3H), 1.42 (s, .5×3H), 1.52 (d, .5×3H), 1.54 (d, .5×3H), 1.61 (s, .5×3H), 1.63 (s, .5×3H), 3.82 (s, 3H), 4.08 (q, .5×2H), 4.18 (q, .5×2H), 4.41 (s, .5×1H), 4.46 (s, .5×1H), 4.52 (dd, 1H), 5.39 (d, 1H), 5.52 (d, .5×1H), 5.54 (d, .5×1H), 6.66–6.82 (m, 1H), 7.06–7.4 (m, 3H) and 7.5–7.8 (m, 1H); |
| $C_2H_5$ | $CH_2O_2CC(CH_3)_3$ | (CDCl₃) 1.17 (s, 9H), 1.39 (s, 3H), 1.46 (t, 3H), 1.61 (s, 3H), 4.12–4.6 (m, 2H), 4.45 (s, 1H), 4.53 (dd, 1H), 5.4 (d, 1H), 5.6 (d, 1H), 5.77 (ab q, 2H), 7.12–7.38 (m, 3H) and 7.6–7.76 (m, 1H); | and

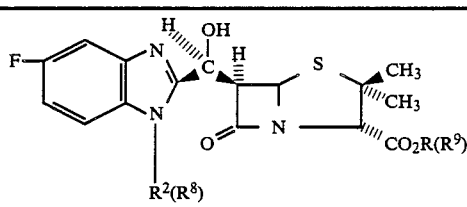

| $R^2(R^8)$ | $R(R^9)$ | NMR(300 MHz), ppm |
|---|---|---|
| $C_2H_5$ | $CH_2O_2CC(CH_3)_3$ | (CDCl₃) 1.43 (s, 3H), 1.47 (t, 3H), 1.64 (s, 3H), 4.16–4.48 (m, 2H), 4.47 (s, 1H), 4.53 (dd, 1H), 5.41 (d, 1H), 5.59 (d, 1H), 5.79 (ab q, 2H), 6.96–7.08 (m, 1H), 7.18–7.28 (m, 1H) and 7.28–7.4 (m, 1H); |
| $C_2H_5$ | $CH_2CN(CH_3)_2$ | (CDCl₃) 1.45 (t, 3H), 1.56 (s, 3H), 1.69 (s, 3H), 2.92 (s, 3H), 2.94 (s, 3H), 3.94–4.56 (m, 3H), 4.51 (s, 1H), 4.78 (ab q, 2H), 5.4 (d, 1H), 5.57 (d, 1H), 6.9–7.1 (m, 1H) and 7.1–7.68 (m, 2H); |
| $C_2H_5$ | $CH(CH_3)OCOCH(CH_3)_2$ | (CDCl₃) 1.12–1.34 (m, 6H), 1.34–1.55 (m, 6H), 1.52 (t, 3H), 1.59 (s, .5 × 3H), 1.62 (s, .5 × 3H), 4.12–4.52 (m, 2H), 4.38 (s, .5 × 1H), 4.43 (s, .5 × 1H), 4.47 (dd, 1H), 4.74–4.90 (m, 1H), 5.37 (d, 1H), 5.55 (d, .5 × 1H), 5.57 (d, .5 × 1H), 6.66–6.8 (m, 1H), 6.9–7.1 (m, 1H), 7.1–7.26 (m, 1H), and 7.26–7.44 (m, 1H); |

-continued

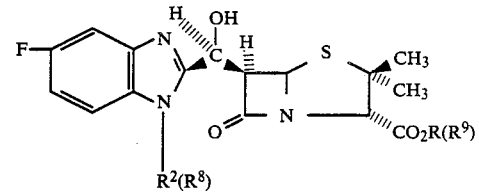

| $R^2(R^8)$ | $R(R^9)$ | NMR(300 MHz), ppm |
|---|---|---|
| $C_2H_5$ | $CH(CH_3)OCOC_2H_5$ | (CDCl₃) 1.29 (t, 3H), 1.38–1.76 (m, 12H), 4.1–4.6 (m, 4H), 4.41 (s, .5 × 1H), 4.46 (s, .5 × 1H), 4.52 (dd, 1H), 5.38 (d, 1H), 5.56 (d, .5 × 1H), 5.58 (d, .5 × 1H), 6.7–6.8 (m, 1H), 6.91–7.08 (m, 1H), 7.08–7.26 (m, 1H) and 7.26–7.36 (m, 1H); |
| $C_2H_5$ | $CH_2O_2CCH_3$ | (CDCl₃) 1.14 (t, 3H), 1.4 (s, 3H), 1.46 (t, 3H), 1.62 (s, 3H), 2.36 (q, 2H), 4.1–4.52 (m, 2H), 4.46 (s, 1H), 4.54 (dd, 1H), 5.38 (d, 1H), 5.56 (d, 1H), 5.78 (ab q, 2H), 6.92–7.12 (m, 1H), 7.12–7.27 (m, 1H) and 7.27–7.4 (m, 1H); |
| $C_2H_5$ | (methyl dioxolenone CH₂ group) | (CDCl₃) 1.34 (s, 3H), 1.45 (t, 3H), 1.62 (s, 3H), 4.12–4.48 (m, 2H), 4.46 (s, 1H), 4.52 (dd, 1H), 4.88 (ab q, 2H), 5.38 (d, 1H), 5.56 (d, 1H), 6.92–7.06 (m, 1H), 7.13–7.24 (m, 1H) and 7.24–7.36 (m, 1H); |

-continued

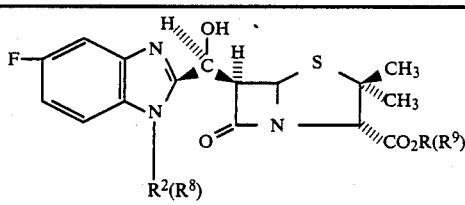

| $R^2(R^8)$ | $R(R^9)$ | NMR(300 MHz), ppm |
|---|---|---|
| CH₃ | CH(CH₃)OCOC₂H₅ (O double bond) | (CDCl₃) 1.37 (t, .5 × 3H), 1.38 (t, .5 × 3H), 1.51 (s, .5 × 3H), 1.52 (s, .5 × 3H), 1.59 (d, .5 × 3H), 1.61 (d, .5 × 3H), 1.69 (s, .5 × 3H), 1.71 (s, .5 × 3H), 3.97 (s, .5 × 3H), 3.98 (s, .5 × 3H), 4.25 (q, .5 × 2H), 4.27 (q, .5 × 2H), 5.54 (d, 1H), 5.64 (d, .5 × 1H), 5.66 (d, .5 × 1H), 6.83 (t, 1H), 7.06–7.16 (m, 1H), 7.26–7.35 (m, 1H) and 7.4–7.46 (m, 1H). |

EXAMPLE 26

5-Carboxyvaleryloxymethyl 6-beta(2-[1-fluoromethylbenzimidazolyl](S)-hydroxy)methylpenicillanate ($R = HO_2C(CH_2)_4CO_2CH_2$—; $R^2 = FCH_2$)

A mixture of 181 mg of 5-benzyloxycarbonyl-valeryloxymethyl 6-beta-(2-[1-fluoromethylbenzimidazolyl]-(S)-hydroxy)methylpenicillanate and 360 mg of prehydrogenated 10% palladium-on-charcoal in 5 ml of water and ml of tetrahydrofuran was shaken in a hydrogen atmosphere at an initial pressure of 45 psi for 3.0 hours. The catalyst was filtered and the filtrate concentrated in vacuo. The residue was extracted and the extracts (3x) concentrated to 140 mg of a clear oil, which was triturated with n-propyl ether and hexane to give 50 mg of solid product.

The NMR (300 MHz-CDCl₃) showed absorption at 1.46 (s, 3H), 1.67 (s, 3H), 1.56–1.64 (m, 4H), 2.28–2.52 (m, 4H), 4.4–4.62 (m, 2H), 5.6 (d, 1H), 5.64 (d, 1H), 5.82 (ab q, 2H), 6.12–6.63 (m, 2H), 7.28–7.72 (m, 3H) and 7.72–7.86 (m, 1H) ppm.

EXAMPLE 27

5-Carboxyvaleryloxymethyl 6-beta (2-[1-ethylbenzimidazolyl](S)-hydroxy)methylpenicillanate ($R^9 = HO_2C(CH_2)_4CO_2CH_2$—; $R^8 = C_2H_5$)

Using the procedure of Example 26, 400 mg of 5-benzyloxycarbonylvaleryloxymethyl 6-beta-(2-[1-methylbenzimidazolyl]-(S)-hydroxy)methylpenicillanate and 800 mg of 10% palladium-on-charcoal gave 50 mg of product.

The NMR (300 MHz-CDCl₃) showed absorption at 1.45 (s, 3H), 1.50 (t, 3H), 1.66 (s, 3H), 1.64–1.84 (m, 4H), 2.28–2.54 (m, 4H), 4.2–4.58 (m, 2H), 4.54 (s, 1H), 4.64 (dd, 1H), 5.43 (d, 1H), 5.59 (d, 1H), 5.82 (ab q, 2H), 7.2–7.6 (m, 3H) and 7.8–7.92 (m, 1H) ppm.

EXAMPLE 28

1-(Ethoxycarbonyloxy)-(S)-ethyl 6-beta-(2-[1-methylbenzimidazolyl]-(S)-hydroxy)methylpenicillanate ($R^9 = (S)C_2H_5OCO_2CH(CH_3)$—; $R^8 = CH_3$)

A. 1-(ethoxycarbonyloxy)-(S)-ethyl 6-(2-[1-methylbenzimidazolyl]hydroxy)methyl-6-bromopenicillanate Employing the procedure of Example 22C, using 8.24 g of 1-(ethoxycarbonyloxy)-(S)-ethyl 6,6-dibromopenicillanate (Example 22B), 6.64 ml of methyl magnesium bromide (2.8M in ether) and 3.28 g of 1-methylbenzimidazole-2-carboxaldehyde gave a quantitative yield of the desired product as a golden oil.

B. 1-(ethoxycarbonyloxy)-(S)-ethyl 6-beta-(2-[1-methylbenzimidazolyl]-(S)-hydroxy)methylpenicillanate Using the procedure of Example 22D, the product of Example 28A and 10 ml of tri-n-butyltin hydride in 125 ml of tetrahydrofuran gave 250 mg of the desired product.

The NMR spectrum (300 MHz-CDCl₃) showed absorption at 1.3 (t, 3H), 1.46 (s, 3H), 1.54 (d, 3H), 1.64 (s, 3H), 3.88 (s, 3H), 4.18 (q, 2H), 4.42 (s, 1H), 4.52 (dd, 1H), 5.46 (d, 1H), 5.58 (d, H), 6.74 (q, 1H), 7.16–7.42 (m, 3H) and 7.64–7.72 (m, 1H) ppm.

PREPARATION A

1-Methoxymethylbenzimidazole-2-carboxaldehyde 1. 1,2-bis(2-benzimidazolyl)-1,2-dihydroxyethane A mixture of 27 g of tartaric acid, 46.72 g of o-phenylenediamine, 45 ml of water, 27 ml of ethanol, 45 ml of 12N hydrochloric acid and 18 ml of 85% phosphoric acid was heated at 135° C. for 12 hours. Water and charcoal were added and the mixture was filtered and made basic with ammonium hydroxide. The solids were filtered, washed with acetone and ether and dried, 43.21 g (67% yield).

2. 1,2-bis(1-methoxymethyl-2-benzimidazolyl)-1,2-dihydroxyethane

To a stirred suspension of 5 g of the product of Preparation A1 in 250 ml of dimethylformamide was added 1.62 g of 50% sodium hydride in oil over a period of ten minutes. After stirring for one hour, 2.56 ml of chloromethylmethyl ether was added over 20 minutes and the reaction mixture allowed to stir at room temperature overnight. The reaction mixture was poured into water and the pH adjusted to 3 with hydrochloric acid. After extracting with chloroform (3×150 ml), the pH was adjusted to 10 with ammonium hydroxide and the product extracted with chloroform (3×150 ml). The extracts were combined, dried over sodium sulfate and concentrated to a yellow oil which was chromatographed on 200 g of silica gel using 4% methanol in chloroform as the eluent. The fractions containing the product were combined and concentrated to an oil which on treatment with ether gave a solid, 1.3 g.

3. 1-methoxymethylbenzimidazole-2-carboxaldehyde

To a solution of 1.3 g of the product of Preparation A2 in 55 ml of 1N sulfuric acid was added 727 mg of sodium meta periodate and the reaction mixture allowed to stir overnight at room temperature. The solution was neutralized with sodium bicarbonate and the product extracted with ethyl acetate (3×75 ml). The extracts were combined, dried over sodium sulfate and concentrated to give 1.2 g of the desired product.

PREPARATION B

1-Methoxyethylbenzimidazole-2-carboxaldehyde

1. 1-methoxyethylbenzimidazole

To a solution of 4.05 g of 1-hydroxyethylbenzimidazole in 25 ml of dimethylformamide was added 1.2 g of 50% sodium hydride in oil, and the mixture stirred for 30 minutes. Methyl iodide (3.55 g) was added and the reaction mixture stirred at room temperature overnight. Water (200 ml) was added and the product extracted with ethyl acetate. The extracts were combined, dried and concentrated to an oil which was chromatographed on 130 g of silica gel using 5% methanol in chloroform as the eluent to give 2.36 g of brown oil.

2. 1-methoxyethylbenzimidazole-2-carboxaldehyde

Following the procedure of Example 1D, 2.36 g of 1-methoxyethylbenzimidazole, 5.15 ml of 2.6M n-butyl lithium in hexane, 1.08 ml of ethyl formate gave on work-up 1.73 g of the desired product as a yellow oil.

PREPARATION C

1-(2-Thienylmethyl)benzimidazole-2-carboxaldehyde

1. 1-(2-thienylmethyl)benzimidazole

To 11.81 g of benzimidazole in 50 ml of dimethylformamide was added 4.8 g of 50% sodium hydride in oil over 30 minutes. After stirring 30 minutes, 13.25 g of 2-chloromethylthiophene was added over a period of 30 minutes, and the reaction mixture stirred at room temperature overnight. The mixture was poured into water and the pH adjusted to 1.5. After extracting with ether, the pH was raised to 11 and precipitated product was filtered and dried, 19.9 g.

2. 1-(2-thienylmethyl)benzimidazole-2-carboxaldehyde

Following the procedure of Example 1D, 10.7 g of the product of Preparation C, 20 ml of 2.5M n-butyl lithium in hexane and 4.03 ml of ethyl formate gave 4.06 g of the desired product as a yellow solid.

PREPARATION D

5,6-Dihydro-4H-imidazo[4,5,1-i,j]quinoline-2-carboxaldehyde

1. 2-methyl-5,6-dihydro-4H-imidazo [4,5,1-i,j]quinoline

A mixture containing 11.08 g of 8-amino-1,2,3,4 tetrahydroquinoline and an equimolar amount of triethylorthoacetate was treated with 50 ml of ethanol and heated to reflux for 4 hours. The ethanol was removed in vacuo and the residue treated with 50 ml toluene and heated at reflux for 10 hours. Two drops of sulfuric acid were added and refluxing continued for 12 hours. The solvent was evaporated and the residue slurried in dilute ammonium hydroxide and extracted with chloroform. The extracts were combined, dried over sodium sulfate and concentrated to a dark solid. The residue was dissolved in ethyl acetate, treated with activated charcoal and the solvent removed to give 6.3 g of product as a tan solid.

2. 5,6-dihydro-4H-imidazo[4,5,1-i,j]quinoline-2-carboxaldehyde

Following the procedure of Example 10B and using 2.58 g of the product of Preparation D1and 1.66 g of selenium dioxide, there was isolated 1.09 g of the desired product as a yellow solid.

PREPARATION E

1-Methylnaphth[2,3-d]imidazole-2-carboxaldehyde

1. 2-methylnaphth[2,3-d]imidazole

To a solution of 4.74 g of 2,3-diaminonaphthalene in 150 ml of ethanol and 30 ml of N,N-dimethylacetamide was added 4.86 g of triethyl orthoacetate, and the mixture heated at 60° C. for 2 hours. An additional 5.5 ml of triethyl orthoacetate was added and stirring continued at 60° C. overnight. The solvent was removed and the residue treated with chloroform. The solids were filtered and the filtrate concentrated to a small volume, treated with ether and filtered. The solids were combined to give 4.07 g of the product as a white solid.

2. 1,2-dimethylnaphth[2,3-d]imidazole

To a suspension of 4.06 g of the product from Preparation E1in 50 ml of dimethylformamide was added portionwise 1.07 g of 50% sodium hydride in oil. After stirring one hour, 1.6 ml of methyl iodide was added and the reaction mixture stirred at room temperature for 2 hours. The mixture was treated with water and the product extracted with ethyl acetate. The extract was dried and the solvent removed in vacuo to give, after washing with hexane, 2.55 g of product.

3. 1-methylnaphth[2,3-d]imidazole-2-carboxaldehyde

Employing the procedure of Example 10B and using 2.56 g of the product of Preparation E2, 1.45 g of selenium dioxide and 100 ml of dioxane, there was obtained 1.89 g of the desired product.

PREPARATION F

3-Methylnaphth[1,2-d]imidazole-2-carboxaldehyde and 1-Methylnaphth[1,2-d]imidazole-2-carboxaldehyde

1. 2-methyl-1H-naphth[1,2-d]imidazole

To a solution of 7.38 g of 1,2-diaminonaphthalene in 175 ml of ethanol was added 8.56 ml of triethyl orthoacetate and the reaction mixture heated to reflux for 3.5 hours. The solvent was removed in vacuo and the residue partitioned between chloroform and water. The organic phase was separated, dried over magnesium sulfate and concentrated to a dark oil, 9.0 g.

2. 1,2-dimethylnaphth[1,2-d]imidazole and 2,3-dimethylnaphth[1,2-d]imidazole To a solution of 8.56 g of 2-methyl-1H-naphth[1,2-d]imidazole in 100 ml of tetrahydrofuran was added over a period of 15 minutes 2.25 g of 50% sodium hydride in oil and the mixture allowed to stir for 20 minutes. Methyl iodide (2.93 ml) was added over a 5-minute period and the reaction mixture allowed to stir at room temperature overnight. The reaction mixture was poured into water and the pH adjusted to 2 with 12N hydrochloric acid. The aqueous acid was extracted with chloroform (2×100 ml) and the pH adjusted to 10 with ammonium hydroxide. The aqueous base was extracted with chloroform (2×100 ml) and the combined extracts dried and concentrated to give 7.75 g of the isomers as a tan solid.

3. 3-methylnaphth[1,2-d]imidazole-2-carboxaldehyde and 1-methylnaphth[1,2-d]imidazole-2-carboxaldehyde Following the procedure of Example 10B and starting with 3.23 g of the isomer mixture of Preparation F2, 1.83 g of selenium dioxide and 75 ml of dioxane, there was obtained, after chromatographing on 200 g of silica gel using 5% ethyl acetate in chloroform eluent, 510 mg of the 3-methyl isomer and 412 mg of the 1-methyl isomer.

PREPARATION G

1-Methylthiomethylbenzimidazole-2-carboxaldehyde 1. 1-methylthiomethyl-2-hydroxymethylbenzimidazole Using the procedure of Preparation $C_1$, 14.8 g of 2-hydroxymethylbenzimidazole, 4.8 g of 50% sodium hydride in oil and 8.36 ml of chloromethyl methyl sulfide in 50 ml of dimethylformamide gave 8.3 g of product.

2. 1-methylthiomethylbenzimidazole-2-carboxaldehyde

To a suspension of 13.9 g of manganese dioxide in 100 ml of methylene chloride was added 3.3 g of the product of Preparation $G_1$ and the reaction mixture stirred at room temperature overnight. The reaction was filtered and the filtrate concentrated to 3 g of product, which was chromatographed on 100 g of silica gel, using 10% ethyl acetate in chloroform as the eluent, to give 2.32 g of product.

PREPARATION H

1-Methyl-5-phenylimidazole-2-carboxaldehyde 1. 1-acetyl-4-phenylimidazole

To a solution of 4-phenylimidazole in 40 ml of tetrahydrofuran was added portionwise 1.66 g of 50% sodium hydride. After stirring for 20 minutes, 2.46 ml of acetyl chloride was added over 10 minutes and the reaction mixture allowed to stir overnight at room temperature. The reaction was filtered and the filtrate concentrated to give 4 g of crude product which was purified by chromatographing on 150 g of silica gel using 5% methanol in chloroform as eluent, 2.88 g.

2. 1-methyl-5-phenylimidazole

To 2.88 g of 1-acetyl-4-phenylimidazole in 50 ml of acetonitrile was added 5.8 ml of methyl iodide and the reaction mixture sealed in a flask over a weekend. The reaction mixture was poured into water and then decanted from insoluble oil. The pH of the decanted solution was adjusted to 9 with sodium carbonate and the solution extracted with chloroform. The extracts were combined, dried over magnesium sulfate and concentrated to give 1.02 g of crude product which was chromatographed on 50 g of silica gel using 30% ethyl acetate in chloroform as the eluent, 640 mg.

3. 1-methyl-5-phenylimidazole-2-carboxaldehyde

Using the procedure of Example 1D, 640 mg of 1-methyl-5-phenylimidazole, 1.55 ml of 2.6M n-butyllithium and 0.31 ml of dimethylformamide gave 320 mg of the desired product.

PREPARATION I 1-(1-Pyrrolyl)-benzimidazole-2-carboxaldehyde

Using the procedure of Example 10B and starting with 1.9 g of 1-(1-pyrrolyl)-2-methylbenzimidazole [Synthesis, 757 (1983)] and 1.07 g of selenium dioxide in 35 ml of dioxane, there was obtained 1.3 g of the product.

PREPARATION J

1-Methyl-1H-imidazo[4,5-c]pyridine-2-carboxaldehyde 1. 2-methyl-1H-imidazo[4,5-c]pyridine A mixture of 5 g of 3,4-diaminopyridine, 3.9 ml of acetic acid and 50 ml of polyphosphoric acid was heated to 125° C. for 2 hours. The reaction mixture was poured into water and the pH adjusted to 8 with ammonium hydroxide. The product was extracted with methanol-chloroform (1:1) and the extracts dried over sodium sulfate and concentrated to dryness. Extraction of the residue with 50 ml of hot ethanol gave 3.98 g of product.

2. 1,2-dimethyl-1H-imidazo[4,5-c]pyridine and 2,3-dimethyl-3H-imidazo[4,5-c]pyridine To a solution of 2-methyl-1H-imidazo[4,5-c]pyridine in 50 ml of dimethylformamide was added 1.43 g of 50% sodium hydride in oil followed, after 20 minutes, by 1.86 ml of methyl iodide. After stirring at room temperature overnight, the solvent was concentrated in vacuo and the residue treated with chloroform and filtered. Removal of the chloroform gave a brown solid which was chromatographed on 150 g of silica gel using 5% methanol in chloroform as the eluent giving 774 mg of a less polar isomer and 356 mg of the desired 1H-imidazo[4,5-c]pyridine isomer.

3. 1-methyl-1H-imidazo[4,5-c]pyridine-2-carboxaldehyde

Using the procedure of Example 10B and starting with 357 mg of 1,2-dimethyl-1H-imidazo[4,5-c]pyridine and 270 mg of selenium dioxide in 30 ml of dioxane, there was obtained 313 mg of the title product.

PREPARATION K

3-Methyl-3H-imidazo[4,5-c]pyridine-2-carboxaldehyde

Employing the procedure of Example 10B and starting with 774 mg of 2,3-dimethyl-3H-imidazo[4,5-c]pyridine (Preparation J2) and 584 mg of selenium dioxide in 30 ml of dioxane, there was obtained 442 mg of the desired product.

PREPARATION L

1-Fluoromethylbenzimidazole-2-carboxaldehyde 1. 1-fluoromethyl-2-methylbenzimidazole To a cold (−78° C.) solution of 2.38 ml of diethylaminosulfur trifluoride in 50 ml of methylene chloride was added over a period of 30 minutes a slurry of 3.0 g of 1-hydroxymethyl-2-methylbenzimidazole in 100 ml of methylene chloride, and the reaction mixture stirred at −78° C. for 20 minutes and at ice bath temperature for 1 hour. The reaction mixture was poured into ice water and the pH adjusted to 7.5–8 with a 6N sodium hydroxide solution. The organic phase was separated and held and the aqueous extracted with methylene chloride (1×75 ml). The extract was combined with the original organic phase, dried over magnesium sulfate and concentrated to a yellow solid, 2.87 g.

2. 1-fluoromethylbenzimidazole-2-carboxaldehyde

Using the procedure of Example 10B and starting with 2.87 g of 1-fluoromethyl-2-methylbenzimidazole and 1.94 g of selenium dioxide in 50 ml of dioxane, 2.58 g of the desired product was isolated.

PREPARATION M

4H-Imidazo[4,5,1-i,j]quinoline-2-carboxaldehyde 1. 2-hydroxymethyl-5,6-dihydro-6-oxo-4H-imidazo[4,5,1-i,j]quinoline To 300 ml of 4N hydrochloric acid was added 12.4 g of 1,2,3,4-tetrahydro-4-oxo-8-aminoquinoline and 12.6 g of 70% glycolic acid and the resulting solution heated to reflux for 24 hours. The solvent was evaporated and the residual red oil was treated with 100 ml water and made basic (pH 9) with sodium carbonate. A black mass was filtered and the product was extracted from the filtrate with chloroform-methanol (3:1). The combined extracts were dried and concentrated to give 2.9 g of an orange-yellow solid.

The black mass was dissolved in methanol, treated with charcoal and concentrated, 4.8 g. The crude product was recrystallized from methanol again to give 1.3 g of a tan solid and 3.4 g of a second crop.

2. 2-hydroxymethyl-5,6-dihydro-6-hydroxy-4H-imidazo[4,5,1-i,j]quinoline

To 2.9 g of the product from Preparation M1 in 100 ml of methanol was added 814 mg of sodium borohydride in 50 ml of methanol and the mixture refluxed for 90 minutes. An additional 814 mg of hydride was added and heating continued for 2 hours. A saturated sodium bicarbonate solution (15 ml) was added and the methanol removed by evaporation. The residue was slurried in ethanol and the mixture filtered. The filtrate was evaporated to dryness and the residue dissolved in methanol, filtered through silica gel and concentrated to give 2.9 g of crude product. The product was purified by recrystallization from methanol-ethyl acetate, 2.98 g.

3. 2-hydroxymethyl-4H-imidazo[4,5,1-i,j]quinoline

A mixture of 2.98 g of the product of Preparation M2, 3 ml of acetic acid and 30 ml of sulfuric acid was heated to reflux for one hour. The mixture was cooled and poured on to ice. Ethyl acetate was added to the ice suspension and the mixture made basic (pH 9) with ammonium hydroxide. The organic phase was separated, dried and concentrated to give 1.9 g of a yellow oil. The oil was taken up in methanol (15 ml), treated with 15 ml of 2N sodium hydroxide solution and the solution stirred for one hour at room temperature. The methanol was evaporated and the product extracted with chloroform, 1.5 g.

4. 4H-imidazo[4,5,1-i,j]quinoline-2-carboxaldehyde

Using the procedure of Preparation G2, 6.3 g of manganese dioxide and 1.35 g of the product of Preparation M3 gave 850 mg of the desired product as a yellow solid.

PREPARATION N

1-Propargylbenzimidazole-2-carboxaldehyde 1. 2-acetoxymethylbenzimidazole

A mixture of 1.0 g of 2-hydroxymethylbenzimidazole and 0.64 ml of acetic anhydride in 10 ml of acetic acid was heated to reflux for 1 hour. The solvent was removed in vacuo and the residue dissolved in chloroform and washed with a sodium bicarbonate solution. The organic layer was separated, dried and concentrated to give 1.2 g of the desired intermediate.

2. 1-propargyl-2-acetoxymethylbenzimidazole

To 1.2 g of the product of Preparation N-1 in 25 ml of dimethylformamide was added 300 mg of 50% sodium hydride followed after 20 minutes by 0.7 ml of propargyl bromide dropwise. After standing for 48 hours, the reaction mixture was diluted with water and the product extracted with ethyl acetate. The organic phase was dried and concentrated to give 1.42 g of product as a yellow oil.

3. 1-propargyl-2-hydroxymethylbenzimidazole

To 19.88 g of the product of Preparation N-2 in 150 ml of methanol was added 5.7 g of potassium hydroxide and the mixture stirred at room temperature overnight. Acetic acid (13 ml) was added and the mixture concentrated to dryness. Water was added and the product extracted with chloroform to give 10.86 g of product.

4. 1-propargylbenzimidazole-2-carboxaldehyde

Using the procedure of Preparation G-2, 10.8 g of the product of Preparation N-3 and 43.5 g of manganese dioxide in 300 ml of methylene chloride and 200 ml of chloroform gave 6.89 g of product.

PREPARATION O

1-Ethyl-5-fluorobenzimidazole-2-carboxaldehyde 1. 1-ethyl-2-methyl-5-fluorobenzimidazole To 2.92 g of N-ethyl-4-fluorophenylenediamine in 15 ml of ethanol was added 3.49 ml of triethylorthoacetate and the reaction refluxed for 6 hours. The solvent was removed and the residue partitioned between ethyl acetate and water. The organic phase was separated, dried and the solvent removed to give 2.87 g of product as a brown oil.

2. 1-ethyl-5-fluorobenzimidazole-2-carboxaldehyde

Using the procedure of Example 10B, 2.87 g of the product of Preparation O1 and 1.78 g of selenium dioxide in 50 ml of dioxane gave 2.05 g of the desired product as a brown oil.

PREPARATION P

1-Fluoromethyl-5- and 6-fluoro benzimidazole-2-carboxaldehyde 1. 1-hydroxymethyl-2-methyl-5- or 6-fluorobenzimidazole Formaldehyde (9.19 ml - 37%) was added to 75 ml of ethanol containing 10.38 g of 2-methyl-5-and 6-fluorobenzimidazole and the reaction refluxed for 6.0 hours. The solvent was removed and the residue triturated with diethyl ether and filtered, 6.4 g.

2. 1-fluoromethyl-2-methyl-5- and 6-fluorobenzimidazole

Using the procedure of Preparation L-1, 6.4 g of the product of Preparation P-1 and 4.69 ml of diethylaminosulfur trifluoride in a total of 200 ml of methylene chloride gave 6.38 g of product.

3. 1-fluoromethyl-5- or 6-fluorobenzimidazole-2-carboxaldehyde

Employing the procedure of Example 10B, the product of Preparation P-2, 6.38 g and 3.89 g of selenium dioxide in 150 ml of dioxane gave 4.56 g of the desired product.

PREPARATION Q

1-Propargyl-5- and 6-fluorobenzimidazole-2-carboxaldehyde

1. 1-propargyl-2-acetoxymethyl-5- and 6-fluorobenzimidazole

Using the procedure of Preparation N-2, 11.11 g of 2-acetoxymethyl-5-fluorobenzimidazole, 2.56 g of 50% sodium hydride and 5.95 ml of propargyl bromide (80% in toluene) in 125 ml of tetrahydrofuran gave 12.2 g of desired product.

2. 1-propargyl-2-hydroxymethyl-5- and 6-fluorobenzimidazole

Employing the procedure of Preparation N-3, the product of Preparation Q-1, 12.2 g, and 3.27 g of potassium hydroxide in 50 ml of methanol gave 8.56 g of the desired product.

3. 1-propargyl-5- and 6-fluorobenzimidazole-2-carboxaldehyde

Following the procedure of Preparation G-2, 4.0 g of the product of Preparation P-2 and 18.53 g of manganese dioxide in 150 ml of methylene chloride gave 3.5 g of product.

PREPARATION R

1-Methyl-5,6-difluorobenzimidazole2-carboxaldehyde

1. 1,2-dimethyl-5,6-difluorobenzimidazole

Using the alkylation procedure of Preparation A-2, 3.6 g of 2-methyl-5,6-difluorobenzimidazole, 1.03 g of 50% sodium hydride and 1.33 ml of methyl iodide in 40 ml of dimethylformamide gave 1.1 g of the desired product as an orange solid.

2. 1-methyl-5,6-difluorobenzimidazole-2-carboxaldehyde

Following the procedure of Example 10B, 1.0 g of the product of Preparation R-1 and 610 mg of selenium dioxide in 50 ml of dioxane gave 931 mg of the desired product.

PREPARATION S

1-Methyl-7-fluorobenzimidazole-2-carboxaldehyde

1. 1,2-dimethyl-7-fluorobenzimidazole

Following the procedure of Preparation O-1, 3.0 g of $N^2$-methyl-3-fluorophenylenediamine and 3.9 ml of triethylorthoacetate in 100 ml of ethanol gave 3.0 g of product.

2. 1-methyl-7-fluorobenzimidazole-2-carboxaldehyde

Employing the procedure of Example 10B, 2.0 g of the product of Preparation S-1 and 1.34 g of selenium dioxide in 50 ml of dioxane gave 1.6 g of the product as a brown solid.

I claim:
1. A compound of the formula

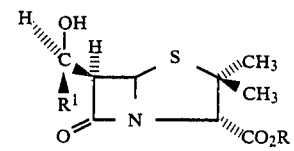

and a pharmaceutically acceptable salt thereof wherein $R^1$ is selected from the group consisting of

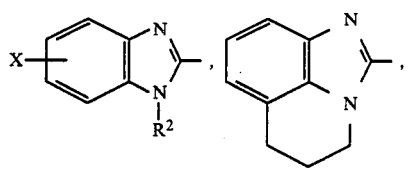

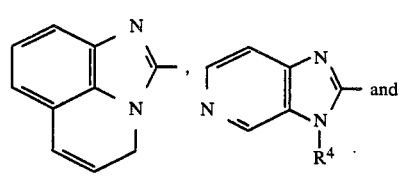

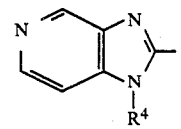

where $R^2$ is selected from the group consisting of propargyl, phenyl, vinyl, allyl, cyclopropyl, fluoromethyl, 2-fluoroethyl, 2-hydroxyethyl, methoxy, methoxymethyl, 2-methoxyethyl, methylthiomethyl and 2-thienylmethyl; $R^4$ is selected from the group consisting of vinyl, allyl and alkyl of one to three carbon atoms; X is selected from the group consisting of hydrogen, methyl, methoxy and fluoro; and R is selected from the group consisting of hydrogen, benzyl, allyl and the residue of an ester group readily hydrolyzable in vivo selected from 3-phthalidyl, 4-crotonolactonyl, gamma-butyrolacton-4-yl,

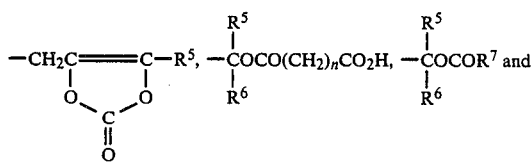

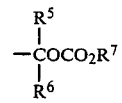

where $R^5$ and $R^6$ are each hydrogen, methyl or ethyl, n is 1 to 5 and $R^7$ is alkyl having one to six carbon atoms.

2. A compound of claim 1, wherein $R^1$ is

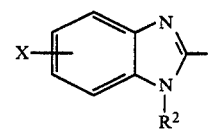

and X and R are each hydrogen.

3. The compound of claim 2, wherein $R^2$ is vinyl.
4. The compound of claim 2, wherein $R^2$ is methylthiomethyl.
5. The compound of claim 2, wherein $R^2$ is allyl.
6. The compound of claim 2, wherein $R^2$ is 2-fluoroethyl.
7. The compound of claim 2, wherein $R^2$ is fluoromethyl.
8. The compound of claim 2, wherein $R^2$ is cyclopropyl.
9. The compound of claim 2, wherein $R^2$ is methoxymethyl.
10. The compound of claim 2, wherein $R^2$ is 2-methoxyethyl.
11. The compound of claim 2, wherein $R^2$ is 2-hydroxyethyl.
12. The compound of claim 2, wherein $R^2$ is 2-thienylmethyl.
13. The compound of claim 2, wherein $R^2$ is methoxy.
14. The compound of claim 2, wherein $R^2$ is propargyl.
15. The compound of claim 1, wherein $R^1$ is

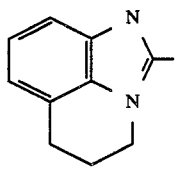

and R is hydrogen.

16. The compound of claim 1, wherein $R^1$ is

and R is hydrogen.

17. A method for treating a bacterial infection in a mammalian subject which comprises administering to said subject an antibacterially effective amount of a compound of the formula

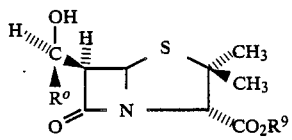

and a pharmaceutically acceptable salt thereof wherein $R°$ is selected from the group consisting of

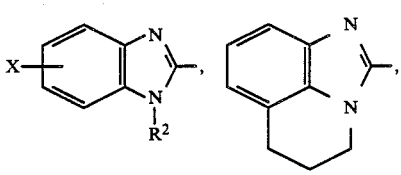

-continued

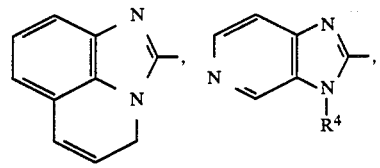

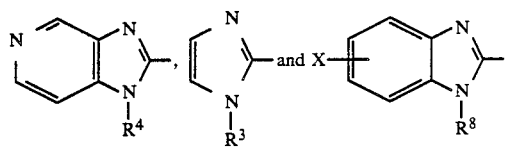

where $R^2$ is selected from the group consisting of propargyl, phenyl, vinyl, allyl, cyclopropyl, fluoromethyl, 2-fluoroethyl, 2-hydroxyethyl, methoxy, methoxymethyl, 2-methoxyethyl, methylthiomethyl and 2-thienylmethyl; $R^3$ is selected from the group consisting of phenyl and vinyl; $R^4$ is selected from the group consisting of vinyl, allyl and alkyl having one to three carbon atoms; X is selected from the group consisting of hydrogen, methyl, methoxy and fluoro; $R^8$ is selected from the group consisting of hydrogen and alkyl having one to three carbon atoms; and $R^9$ is selected from the group consisting of hydrogen and the residue of an ester group readily hydrolyzable in vivo selected from 3-phthalidyl, 4-crotonolactonyl, gamma-butyrolacton-4-yl,

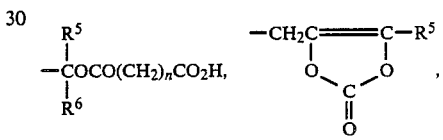

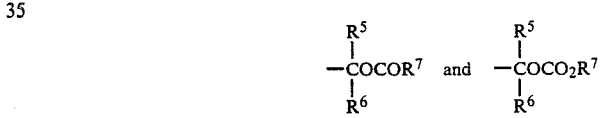

where $R^5$ and $R^6$ are each hydrogen, methyl or ethyl, n is 1 to 5 and $R^7$ is alkyl having one to six carbon atoms.

18. The method of claim 17, wherein $R°$ is

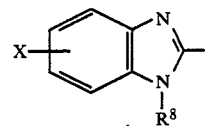

and X and $R^9$ are each hydrogen.

19. The method of claim 17, wherein $R^8$ is ethyl.
20. The method of claim 17, wherein $R^8$ is n-propyl.
21. The method of claim 17, wherein $R°$ is

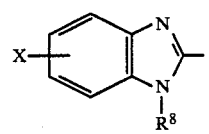

and $R^9$ is hydrogen and $R^8$ is methyl.

22. The method of claim 21, wherein X is hydrogen.
23. The method of claim 21, wherein X is 6-methyl.
24. The method of claim 21, wherein X is 7-methyl.
25. The method of claim 21, wherein X is 5-methoxy.
26. The method of claim 21, wherein X is 5-methyl.
27. The method of claim 21, wherein X is 5-fluoro.